United States Patent
Kufe et al.

(10) Patent No.: US 10,617,773 B2
(45) Date of Patent: Apr. 14, 2020

(54) ANTIBODIES AGAINST THE MUC1-C/EXTRACELLULAR DOMAIN (MUC1-C/ECD)

(71) Applicants: DANA-FARBER CANCER INSTITUTE, INC., Boston, MA (US); GENUS ONCOLOGY, LLC, Chicago, IL (US)

(72) Inventors: Donald W. Kufe, Wellesley, MA (US); Surender Kharbanda, Natick, MA (US)

(73) Assignees: DANA-FARBER CANCER INSTITUTE, INC., Boston, MA (US); GENUS ONCOLOGY, LLC, Chicago, IL (US)

( * ) Notice: Subject to any disclaimer, the term of this patent is extended or adjusted under 35 U.S.C. 154(b) by 0 days.

(21) Appl. No.: 15/663,951

(22) Filed: Jul. 31, 2017

(65) Prior Publication Data
US 2018/0036441 A1 Feb. 8, 2018

Related U.S. Application Data

(60) Provisional application No. 62/371,320, filed on Aug. 5, 2016.

(51) Int. Cl.
*A61K 39/39* (2006.01)
*A61K 51/10* (2006.01)
*A61K 39/395* (2006.01)
*A61K 47/68* (2017.01)
*C07K 16/30* (2006.01)
*A61K 39/00* (2006.01)

(52) U.S. Cl.
CPC ............ *A61K 51/10* (2013.01); *A61K 39/395* (2013.01); *A61K 47/6803* (2017.08); *A61K 47/6849* (2017.08); *C07K 16/3092* (2013.01); *A61K 2039/505* (2013.01); *C07K 2317/24* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 7,202,346 B2 | 4/2007 | Payne et al. |
| 7,897,351 B2 | 3/2011 | Wreschner et al. |
| 8,344,113 B2 | 1/2013 | Bamdad |
| 2004/0057952 A1 | 3/2004 | Payne et al. |
| 2016/0340442 A1 | 11/2016 | Kufe et al. |

FOREIGN PATENT DOCUMENTS

| WO | WO 1991/016353 | 10/1991 |
| WO | WO 2004/005470 | 1/2004 |

OTHER PUBLICATIONS

Paul, Fundamental Immunology, 3rd Edition, 1993, pp. 292-295 (Year: 1993).*
Casset et al. (BBRC 307, 198-205 2003 (Year: 2003).*
Pascalis et al., (The Journal of Immunology vol. 169, 3076-3084, 2002 (Year: 2002).*
Rudikoff et al., (Proc. Natl. Acad. Sci. USA 1982 vol. 79: p. 1979 (Year: 1979).*
Hartman et al., "MUC1 isoform specific monoclonal antibody 6E6/2 detects preferential expression of the novel MUC1/Y protein in breast and ovarian cancer," *Int. J. Cancer*, 82:256-267, 1999.
PCT International Search Report and Writen Opinion issued in International Application No. PCT/US2015/013410, dated Jul. 3, 2015.
PCT Invitation to Pay Additional Fees issued in International Application No. PCT/US2015/013410, dated Apr. 28, 2015.
Pichinuk et al., "Antibody targeting of cell-bound MUC1 SEA domain kills tumor cells," *Cancer Research*, 72(13):3324-3336, 2012.

* cited by examiner

*Primary Examiner* — Lei Yao
(74) *Attorney, Agent, or Firm* — Parker Highlander PLLC

(57) ABSTRACT

The present disclosure is directed to antibodies binding to MUC1-C/extracellular domain (MUC1-C/ECD) and methods of using such antibodies to treat cancers that express the MUC1 antigen.

16 Claims, 13 Drawing Sheets

Specification includes a Sequence Listing.

Figure 6 Affinity ranking of humanized antibodies using Biacore T200.

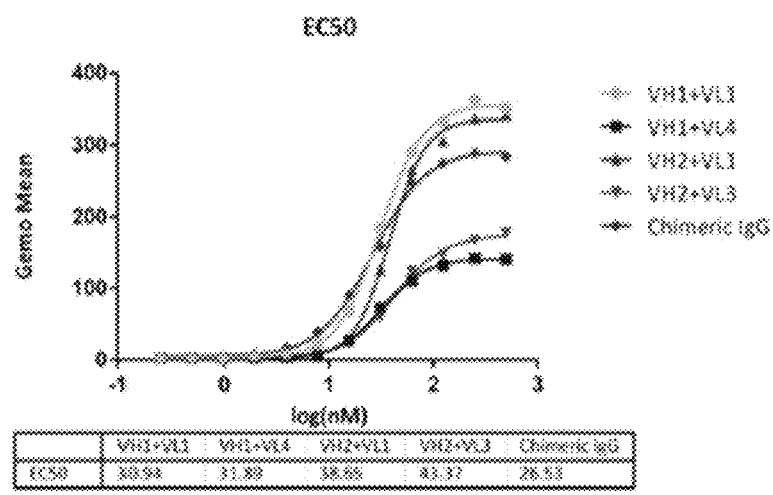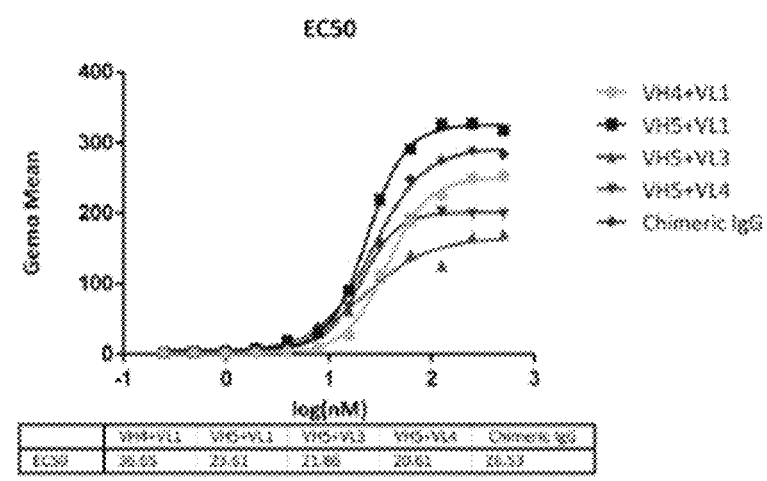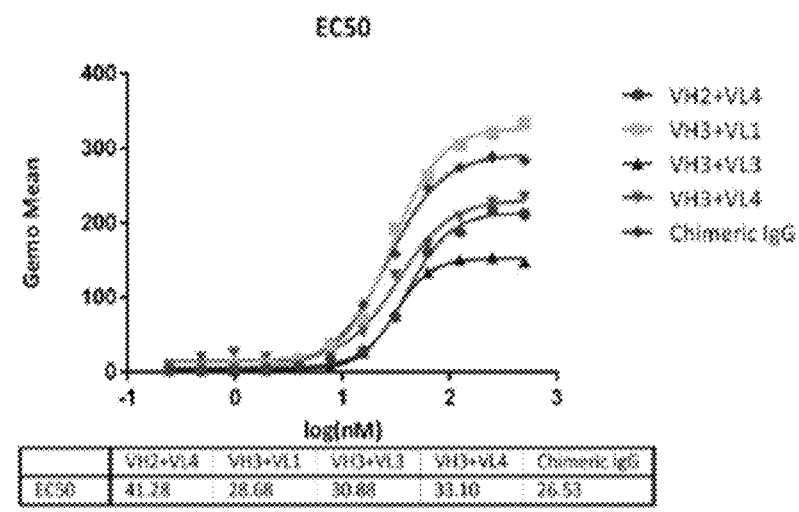
FIG. 8

VH1 – SEQ ID NO: 18

*MGWSWILLFLLSVTAGVHS*QVQLVQSGAEVKKPGSSVKVSCKASGYAFSNFWMNWV
RQAPGQGLEWMGQIYPGDGDTNYNGKFKGRVTITADKSTSTAYMELSSLRSEDTA
VYYCARSYYRSAWFAYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGK*

VH1 – SEQ ID NO: 19 gccgccacc*ATGGGCTGGAGCTGGATCCTGCTGTTCCTCCTGAGCGTGACAGCAGGAGTGCA
CAG*CCAGGTGCAGCTGGTCCAGAGCGGGGCAGAAGTGAAAAAGCCAGGGTCAA
GTGTGAAGGTCTCATGTAAAGCAAGCGGATACGCATTTAGCAACTTCTGGATG
AATTGGGTGAGGCAGGCACCAGGACAGGGCCTGGAGTGGATGGGCCAGATCT
ACCCTGGCGACGGCGATACCAACTATAATGGCAAGTTTAAGGGCCGGGTGACC
ATCACAGCCGACAAGTCTACCAGCACAGCCTACATGGAGCTGAGCTCCCTGCG
GTCCGAGGATACAGCCGTGTACTATTGCGCCAGATCTTATTACAGATCAGCATG
GTTCGCATACTGGGGGCAGGGGACACTGGTCACCGTCTCATCCGCTAGCACCAA
GGGCCCATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGCACCCAGA
CCTACATCTGCAACGTGAATCACAAGCCCAGCAACACCAAGGTGGACAAGAAAGTT
GAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATC
TCCCGGACCCCTGAGGTCACATGCGTGGTGGTGGACGTGAGCCACGAAGACCCTGA
GGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTG
CACCAGGACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAGAACCAC
AGGTGTACACCCTGCCCCCATCCCGGGATGAGCTGACCAAGAACCAGGTCAGCCTG
ACCTGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACGGCT
CCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGC
CTCTCCCTGTCTCCGGGTAAATGA

FIG. 9

VH2 – SEQ ID NO: 20

*MGWSWILLFLLSVTAGVHS*QVQLVQSGAEVKKPGASVKVSCKASGYAFSNFWMNWV
RQAPGQGLEWMGQIYPGDGDTNYNGKFKGRVTMTRDTSTSTVYMELSSLRSEDT
AVYYCARSYYRSAWFAYWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKS
LSLSPGK*

VH2 – SEQ ID NO: 21 gccgccacc*ATGGGCTGGAGCTGGATCCTGCTGTTCCTCCTGAGCGTGACAGCAGGAGTGCA
CAGCC*AGGTCCAGCTGGTGCAGTCAGGAGCAGAAGTGAAAAAACCCGGCGCAT
CAGTGAAAGTGTCTTGTAAAGCATCAGGCTACGCATTTAGCAACTTCTGGATGA
ATTGGGTGCGGCAGGCACCAGGACAGGGCCTGGAGTGGATGGGCCAGATCTA
CCCTGGCGACGGCGATACAAACTATAATGGCAAGTTTAAGGGCCGGGTGACCA
TGACAAGAGACACCTCTACAAGCACCGTGTACATGGAGCTGAGCTCCCTGAGG
TCCGAGGATACCGCCGTGTACTATTGCGCCCGCTCTTACTATCGCTCCGCTTGG
TTCGCTTATTGGGGACAGGGGACACTGGTCACCGTCTCCTCAGCTAGCACCAAG
GGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGA
GCCCAAATCTTGTGACAAAACTCACACATGCCCACCGTGCCCAGCACCTGAACTCCT
GGGGGGACCGTCAGTCTTCCTCTTCCCCCCAAAACCCAAGGACACCCTCATGATCTC
CCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCG
CGGGAGGAGCAGTACAACAGCACGTACCGTGTGGTCAGCGTCCTCACCGTCCTGCA
CCAGGACTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGAC
CTGCCTGGTCAAAGGCTTCTATCCAGCGACATCGCCGTGGAGTGGGAGAGCAATG
GGCAGCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGAACGT
CTTCTCATGCTCCGTGATGCATGAGGCTCTGCACAACCACTACACGCAGAAGAGCCT
CTCCCTGTCTCCGGGTAAATGA

FIG. 10

VH3 – SEQ ID NO: 22

*MGWSWILLFLLSVTAGVHS*QVQLVQSGAEVKKPGASVKVSCKASGYAFSNFWMNWV
RQAPGQGLEWMGQIYPGDGDTNYNGKFKGRVTMTRDTSISTAYMELSRLRSDDT
AVYYCARSYYRSAWFAYWGQGTLVTVSS<u>ASTKGPSVFPLAPSSKSTSGGTAALGCLV
KDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKS
LSLSPGK</u>*

VH3 – SEQ ID NO: 23

*gccgccacc**ATGGGCTGGAGCTGGATCCTGCTGTTCCTCCTGAGCGTGACAGCAGGAGTGCA
CAG**CCAGGTCCAGCTGGTGCAGAGTGGGGCAGAAGTGAAGAAACCCGGAGCAA
GTGTCAAAGTGTCCTGTAAGGCAAGCGGATACGCATTTTCCAACTTCTGGATGA
ATTGGGTGCGGCAGGCACCAGGACAGGGCCTGGAGTGGATGGGCCAGATCTA
CCCTGGCGACGGCGATACCAACTATAATGGCAAGTTTAAGGGCAGGGTGACCA
TGACACGCGACACCAGCATCTCCACAGCCTACATGGAGCTGTCTCGGCTGAGA
AGCGACGATACAGCCGTGTACTATTGCGCCAGGTCTTATTATCGCTCTGCTTGG
TTCGCCTACTGGGGACAGGGCACTCTGGTCACCGTCTCCTCT<u>GCTAGCACCAAG
GGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGA
GCCCAAATCTTGTGACAAAACTCACACATGCCCACCGTGCCCAGCACCTGAACTCCT
GGGGGGACCGTCAGTCTTCCTCTTCCCCCCAAAACCCAAGGACACCCTCATGATCTC
CCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCG
CGGGAGGAGCAGTACAACAGCACGTACCGTGTGGTCAGCGTCCTCACCGTCCTGCA
CCAGGACTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGAC
CTGCCTGGTCAAAGGCTTCTATCCAGCGACATCGCCGTGGAGTGGGAGAGCAATG
GGCAGCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGAACGT
CTTCTCATGCTCCGTGATGCATGAGGCTCTGCACAACCACTACACGCAGAAGAGCCT
CTCCCTGTCTCCGGGTAAATGA</u>*

FIG. 11

VH5 – SEQ ID NO: 24

*MGWSWILLFLLSVTAGVHS*EVQLVQSGAEVKKPGESLKISCKGSGYAFSNFWMNWVR
QMPGKGLEWMGQIYPGDGDTNYNGKFKGQVTISADKSISTAYLQWSSLKASDTA
MYYCARSYYRSAWFAYWGQGTLVTVSLASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGK*

VH5 – SEQ ID NO: 25 gccgccacc*ATGGGCTGGAGCTGGATCCTGCTGTTCCTCCTGAGCGTGACAGCAGGAGTGCA
CAGC*GAAGTGCAGCTGGTGCAGTCTGGCGCTGAAGTGAAGAAACCTGGCGAAA
GCCTGAAGATTAGTTGTAAAGGGTCTGGATACGCATTCAGCAACTTCTGGATG
AATTGGGTGCGGCAGATGCCAGGCAAGGGCCTGGAGTGGATGGGACAGATCT
ACCCTGGCGACGGCGATACCAACTATAATGGCAAGTTTAAGGGCCAGGTGACC
ATCTCCGCCGACAAGTCTATCAGCACAGCCTACCTGCAGTGGAGCTCCCTGAA
GGCCTCCGATACAGCCATGTACTATTGCGCCAGATCTTACTATCGCTCCGCTTG
GTTCGCATACTGGGGCAGGGCACTCTGGTCACCGTGTCACTGGCTAGCACCAA
GGGCCCATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGCACCCAGA
CCTACATCTGCAACGTGAATCACAAGCCCAGCAACACCAAGGTGGACAAGAAAGTT
GAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATC
TCCCGGACCCCTGAGGTCACATGCGTGGTGGTGGACGTGAGCCACGAAGACCCTGA
GGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTG
CACCAGGACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAGAACCAC
AGGTGTACACCCTGCCCCCATCCCGGGATGAGCTGACCAAGAACCAGGTCAGCCTG
ACCTGCCTGGTCAAAGGCTTCTATCCAGCGACATCGCCGTGGAGTGGGAGAGCAA
TGGGCAGCCGGAGAACAACTACAAGACCACGCCTCCCGTGCTGGACTCCGACGGCT
CCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGC
CTCTCCCTGTCTCCGGGTAAATGA

FIG. 12

VL1 – SEQ ID NO: 26

*MGWSWILLFLLSVTAGVHS*EIVLTQSPDFQSVTPKEKVTITCRASQSIGTSIHWYQQKP
DQSPKLLIKYASESISGVPSRFSGSGSGTDFTLTINSLEAEDAATYYCQQSNNWPLTF
GQGTKVEIK<u>RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC</u>*

VL1 – SEQ ID NO: 27 gccgccacc*ATGGGCTGGAGCTGGATCCTGCTGTTCCTCCTGAGCGTGACAGCAGGAGTGCA
CAGC*GAGATTGTGCTGACTCAGAGTCCAGACTTCCAGTCAGTGACCCCCAAGGA
GAAAGTCACCATCACATGCCGGGCAAGCCAGTCCATCGGCACAAGCATTCACT
GGTACCAGCAGAAGCCCGATCAGTCCCTAAGCTGCTGATCAAATATGCCTCT
GAAAGTATTTCAGGGGTGCCCTCTAGATTCAGCGGCTCCGGGTCTGGAACAGA
CTTTACTCTGACCATTAACTCCCTGGAGGCTGAAGATGCCGCTACTTACTATTG
TCAGCAGAGCAATAACTGGCCTCTGACATTCGGGCAGGGGACCAAAGTGGAAA
TCAAA<u>CGAACGGTGGCTGCACCATCTGTCTTCATCTTCCCGCCATCTGATGAGCAGT
TGAAATCTGGAACTGCCTCTGTTGTGTGCCTGCTGAATAACTTCTATCCCAGAGAGG
CCAAAGTACAGTGGAAGGTGGATAACGCCCTCCAATCGGGTAACTCCCAGGAGAGT
GTCACAGAGCAGGACAGCAAGGACAGCACCTACAGCCTCAGCAGCACCCTGACGCT
GAGCAAAGCAGACTACGAGAAACACAAAGTCTACGCCTGCGAAGTCACCCATCAGG
GCCTGAGCTCGCCCGTCACAAAGAGCTTCAACAGGGGAGAGTGTTAG</u>

FIG. 13

VH4 – SEQ ID NO: 28

*MGWSWILLFLLSVTAGVHS*QVQLVQSGAEVKKPGATVKISCKVSGYAFSNFWMNWV
QQAPGKGLEWMGQIYPGDGDTNYNGKFKGRVTITADTSTDTAYMELSSLRSEDTA
VYYCARSYYRSAWFAYWGQGTLVTVSRASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGK*

VL2 – SEQ ID NO: 29

*MGWSWILLFLLSVTAGVHS*EIVMTQSPATLSVSPGERATLSCRASQSIGTSIHWYQQKP
GQAPRLLIYYASESISGIPARFSGSGSGTEFTLTISSLQSEDFAVYYCQQSNNWPLTF
GGGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC*

VL3 – SEQ ID NO: 30

*MGWSWILLFLLSVTAGVHS*EIVLTQSPATLSLSPGERATLSCRASQSIGTSIHWYQQKP
GQAPRLLIYYASESISGIPARFSGSGSGTDFTLTISSLEPEDFAVYYCQQSNNWPLTF
GGGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC*

VL4 – SEQ ID NO: 31

*MGWSWILLFLLSVTAGVHS*AIQLTQSPSSLSASVGDRVTITCRASQSIGTSIHWYQQKPG
KAPKLLIYYASESISGVPSRFSGSGSGTDFTLTISSLQPEDFATYYCQQSNNWPLTFG
GGTKVEIKRTVAAPSVFIFPPSDEQLKSGTASVVCLLNNFYPREAKVQWKVDNALQSG
NSQE SVTEQDSKDSTYSLSSTLTLSKADYEKHKVYACEVTHQGLSSPVTKSFNRGEC*

VL5 – SEQ ID NO: 32

*MGWSWILLFLLSVTAGVHS*DIVMTQSPSLLSASTGDRVTISCRASQSIGTSIHWYQQKP
GKAPELLIYYASESISGVPSRFSGSGSGTDFTLTISCLQSEDFATYYCQQSNNWPLTF
GQGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC*

FIG. 14

SEQUENCE LISTING

```
<160> NUMBER OF SEQ ID NOS: 45

<210> SEQ ID NO 1
<211> LENGTH: 158
<212> TYPE: PRT
<213> ORGANISM: Homo sapiens

<400> SEQUENCE: 1

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr Asn Leu Thr Ile Ser Asp Val Ser Val Ser Asp Val Pro
        35                  40                  45

Phe Pro Phe Ser Ala Gln Ser Gly Ala Gly Val Pro Gly Trp Gly Ile
    50                  55                  60
```

```
Ala Leu Leu Val Leu Val Cys Val Leu Val Ala Leu Ala Ile Val Tyr
 65                  70                  75                  80

Leu Ile Ala Leu Ala Val Cys Gln Cys Arg Arg Lys Asn Tyr Gly Gln
                 85                  90                  95

Leu Asp Ile Phe Pro Ala Arg Asp Thr Tyr His Pro Met Ser Glu Tyr
            100                 105                 110

Pro Thr Tyr His Thr His Gly Arg Tyr Val Pro Pro Ser Ser Thr Asp
        115                 120                 125

Arg Ser Pro Tyr Glu Lys Val Ser Ala Gly Asn Gly Gly Ser Ser Leu
130                 135                 140

Ser Tyr Thr Asn Pro Ala Val Ala Ala Thr Ser Ala Asn Leu
145                 150                 155

<210> SEQ ID NO 2
<211> LENGTH: 107
<212> TYPE: PRT
<213> ORGANISM: Artificial sequence
<220> FEATURE:
<223> OTHER INFORMATION: Synthetic peptide

<400> SEQUENCE: 2

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys
            100                 105

<210> SEQ ID NO 3
<211> LENGTH: 119
<212> TYPE: PRT
<213> ORGANISM: Artificial sequence
<220> FEATURE:
<223> OTHER INFORMATION: Synthetic peptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
```

Thr Leu Val Thr Val Ser Ser
        115

<210> SEQ ID NO 4
<211> LENGTH: 119
<212> TYPE: PRT
<213> ORGANISM: Artificial sequence
<220> FEATURE:
<223> OTHER INFORMATION: Synthetic peptide

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial sequence
<220> FEATURE:
<223> OTHER INFORMATION: Synthetic peptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial sequence
<220> FEATURE:

<223> OTHER INFORMATION: Synthetic peptide

<400> SEQUENCE: 6

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Phe
            20                  25                  30

Trp Met Asn Trp Val Arg Gln Met Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Leu
        115
```

<210> SEQ ID NO 7
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 7

```
gagattgtgc tgactcagag tccagacttc cagtcagtga cccccaagga gaaagtcacc      60
atcacatgcc gggcaagcca gtccatcggc acaagcattc actggtacca gcagaagccc    120
gatcagtccc ctaagctgct gatcaaatat gcctctgaaa gtatttcagg ggtgccctct    180
agattcagcg gctccgggtc tggaacagac tttactctga ccattaactc cctggaggct    240
gaagatgccg ctacttacta ttgtcagcag agcaataact ggcctctgac attcgggcag    300
gggaccaaag tggaaatcaa a                                               321
```

<210> SEQ ID NO 8
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 8

```
caggtgcagc tggtccagag cggggcagaa gtgaaaaagc cagggtcaag tgtgaaggtc       60
tcatgtaaag caagcggata cgcatttagc aacttctgga tgaattgggt gaggcaggca    120
ccaggacagg gcctggagtg gatgggccag atctaccctg gcgacggcga taccaactat    180
aatggcaagt ttaagggccg ggtgaccatc acagccgaca gtctaccag cacagcctac     240
atggagctga gctccctgcg gtccgaggat acagccgtgt actattgcgc cagatcttat    300
tacagatcag catggttcgc atactggggg caggggacac tggtcaccgt ctcatcc       357
```

<210> SEQ ID NO 9
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 9

```
caggtccagc tggtgcagtc aggagcagaa gtgaaaaaac ccggcgcatc agtgaaagtg    60
tcttgtaaag catcaggcta cgcatttagc aacttctgga tgaattgggt gcggcaggca   120
ccaggacagg gcctggagtg gatgggccag atctaccctg cgacggcga tacaaactat   180
aatggcaagt ttaagggccg ggtgaccatg acaagagaca cctctacaag caccgtgtac   240
atggagctga gctccctgag gtccgaggat accgccgtgt actattgcgc cgctcttac   300
tatcgctccg cttggttcgc ttattgggga caggggacac tggtcaccgt ctcctca     357
```

<210> SEQ ID NO 10
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 10

```
caggtccagc tggtgcagag tggggcagaa gtgaagaaac ccggagcaag tgtcaaagtg    60
tcctgtaagg caagcggata cgcatttttcc aacttctgga tgaattgggt gcggcaggca   120
ccaggacagg gcctggagtg gatgggccag atctaccctg cgacggcga taccaactat   180
aatggcaagt ttaagggcag ggtgaccatg acacgcgaca ccagcatctc cacagcctac   240
atggagctgt ctcggctgag aagcgacgat acagccgtgt actattgcgc caggtcttat   300
tatcgctctg cttggttcgc ctactgggga cagggcactc tggtcaccgt ctcctct     357
```

<210> SEQ ID NO 11
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 11

```
gaagtgcagc tggtgcagtc tggcgctgaa gtgaagaaac ctggcgaaag cctgaagatt    60
agttgtaaag ggtctggata cgcattcagc aacttctgga tgaattgggt gcggcagatg   120
ccaggcaagg gcctggagtg gatgggacag atctaccctg cgacggcga taccaactat   180
aatggcaagt ttaagggcca ggtgaccatc tccgccgaca gtctatcag cacagcctac   240
ctgcagtgga gctccctgaa ggcctccgat acagccatgt actattgcgc cagatcttac   300
tatcgctccg cttggttcgc atactggggg cagggcactc tggtcaccgt gtcactg     357
```

<210> SEQ ID NO 12
<211> LENGTH: 58
<212> TYPE: PRT
<213> ORGANISM: Artificial sequence
<220> FEATURE:
<223> OTHER INFORMATION: Synthetic peptide

<400> SEQUENCE: 12

```
Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr Asn Leu Thr Ile Ser Asp Val Ser Val Ser Asp Val Pro
        35                  40                  45

Phe Pro Phe Ser Ala Gln Ser Gly Ala Gly
```

<210> SEQ ID NO 13
<211> LENGTH: 107
<212> TYPE: PRT
<213> ORGANISM: Artificial sequence
<220> FEATURE:
<223> OTHER INFORMATION: Synthetic peptide

<400> SEQUENCE: 13

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Asn Trp Pro Leu
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Artificial sequence
<220> FEATURE:
<223> OTHER INFORMATION: Synthetic peptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Asn Trp Pro Leu
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial sequence
<220> FEATURE:
<223> OTHER INFORMATION: Synthetic peptide

<400> SEQUENCE: 15

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Ser
            20                  25                  30

Ile His Trp Tyr Gln Gln Lys Pro Gly Lys Ala Pro Lys Leu Leu Ile
            35                  40                  45

Tyr Tyr Ala Ser Glu Ser Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Asn Trp Pro Leu
                 85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial sequence
<220> FEATURE:
<223> OTHER INFORMATION: Synthetic peptide

<400> SEQUENCE: 16

Asp Ile Val Met Thr Gln Ser Pro Ser Leu Ser Ala Ser Thr Gly
 1               5                  10                  15

Asp Arg Val Thr Ile Ser Cys Arg Ala Ser Gln Ser Ile Gly Thr Ser
                 20                  25                  30

Ile His Trp Tyr Gln Gln Lys Pro Gly Lys Ala Pro Glu Leu Leu Ile
            35                  40                  45

Tyr Tyr Ala Ser Glu Ser Ile Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Ser Asn Asn Trp Pro Leu
                 85                  90                  95

Thr Phe Gly Gln Gly Thr Lys Val Glu Ile Lys
            100                 105

<210> SEQ ID NO 17
<211> LENGTH: 119
<212> TYPE: PRT
<213> ORGANISM: Artificial sequence
<220> FEATURE:
<223> OTHER INFORMATION: Synthetic peptide

<400> SEQUENCE: 17

Gln Val Gln Leu Val Gln Ser Gly Ala Glu Val Lys Lys Pro Gly Ala
 1               5                  10                  15

Thr Val Lys Ile Ser Cys Lys Val Ser Gly Tyr Ala Phe Ser Asn Phe
                 20                  25                  30

Trp Met Asn Trp Val Gln Gln Ala Pro Gly Lys Gly Leu Glu Trp Met
            35                  40                  45

Gly Gln Ile Tyr Pro Gly Asp Gly Asp Thr Asn Tyr Asn Gly Lys Phe
 50                  55                  60

Lys Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Tyr Tyr Arg Ser Ala Trp Phe Ala Tyr Trp Gly Gln Gly
            100                 105                 110

Thr Leu Val Thr Val Ser Arg

-continued

115

<210> SEQ ID NO 18
<211> LENGTH: 468
<212> TYPE: PRT
<213> ORGANISM: Artificial sequence
<220> FEATURE:
<223> OTHER INFORMATION: Synthetic peptide

<400> SEQUENCE: 18

```
Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Ala Phe
        35                  40                  45

Ser Asn Phe Trp Met Asn Trp Val Arg Gln Ala Pro Gly Gln Gly Leu
    50                  55                  60

Glu Trp Met Gly Gln Ile Tyr Pro Gly Asp Gly Asp Thr Asn Tyr Asn
65                  70                  75                  80

Gly Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Tyr Tyr Arg Ser Ala Trp Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
```

```
              355                 360                 365
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 19
<211> LENGTH: 1416
<212> TYPE: DNA
<213> ORGANISM: Artificial sequence
<220> FEATURE:
<223> OTHER INFORMATION: Synthetic oligonucleotide

<400> SEQUENCE: 19
gccgccacca tgggctggag ctggatcctg ctgttcctcc tgagcgtgac agcaggagtg      60
cacagccagg tgcagctggt ccagagcggg gcagaagtga aaaagccagg gtcaagtgtg     120
aaggtctcat gtaaagcaag cggatacgca tttagcaact tctggatgaa ttgggtgagg     180
caggcaccag acagggcct ggagtggatg ggccagatct accctggcga cggcgatacc      240
aactataatg gcaagtttaa gggccgggtg accatcacag ccgacaagtc taccagcaca     300
gcctacatgg agctgagctc cctgcggtcc gaggatacag ccgtgtacta ttgcgccaga     360
tcttattaca gatcagcatg gttcgcatac tgggggcagg ggacactggt caccgtctca     420
tccgctagca ccaagggccc atcggtcttc cccctggcac cctcctccaa gagcacctct     480
gggggcacag cggccctggg ctgcctggtc aaggactact tccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780
ggaccgtcag tcttcctctt ccccccaaaa cccaaggaca cctcatgat ctccggacc      840 cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagccc cgagaaccca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
```

-continued

```
acgcagaaga gcctctccct gtctccgggt aaatga                                    1416
```

<210> SEQ ID NO 20
<211> LENGTH: 468
<212> TYPE: PRT
<213> ORGANISM: Artificial sequence
<220> FEATURE:
<223> OTHER INFORMATION: Synthetic peptide

<400> SEQUENCE: 20

Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Ser Asn Phe Trp Met Asn Trp Val Arg Gln Ala Pro Gly Gln Gly Leu
    50                  55                  60

Glu Trp Met Gly Gln Ile Tyr Pro Gly Asp Gly Asp Thr Asn Tyr Asn
65                  70                  75                  80

Gly Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Tyr Tyr Arg Ser Ala Trp Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln

```
                355                 360                 365
Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465
```

<210> SEQ ID NO 21
<211> LENGTH: 1416
<212> TYPE: DNA
<213> ORGANISM: Artificial sequence
<220> FEATURE:
<223> OTHER INFORMATION: Synthetic oligonucleotide

<400> SEQUENCE: 21

```
gccgccacca tgggctggag ctggatcctg ctgttcctcc tgagcgtgac agcaggagtg      60
cacagccagg tccagctggt gcagtcagga gcagaagtga aaaaacccgg cgcatcagtg     120
aaagtgtctt gtaaagcatc aggctacgca tttagcaact tctggatgaa ttgggtgcgg     180
caggcaccag acagggcct ggagtggatg ggccagatct accctggcga cggcgataca      240
aactataatg gcaagtttaa gggccgggtg accatgacaa gagacacctc tacaagcacc     300
gtgtacatgg agctgagctc cctgaggtcc gaggataccg ccgtgtacta ttgcgcccgc     360
tcttactatc gctccgcttg gttcgcttat tggggacagg ggacactggt caccgtctcc     420
tcagctagca ccaagggccc atcggtcttc cccctggcac cctcctccaa gagcacctct     480
gggggcacag cggccctggg ctgcctggtc aaggactact tccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780
ggaccgtcag tcttcctctt ccccccaaaa cccaaggaca cctcatgat  ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagccc cgagaaccca ggtgtacacc ctgccccca atcccgggat     1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
```
acgcagaaga gcctctccct gtctccgggt aaatga                                    1416

<210> SEQ ID NO 22
<211> LENGTH: 468
<212> TYPE: PRT
<213> ORGANISM: Artificial sequence
<220> FEATURE:
<223> OTHER INFORMATION: Synthetic peptide

<400> SEQUENCE: 22

```
Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Ser Asn Phe Trp Met Asn Trp Val Arg Gln Ala Pro Gly Gln Gly Leu
    50                  55                  60

Glu Trp Met Gly Gln Ile Tyr Pro Gly Asp Gly Asp Thr Asn Tyr Asn
65                  70                  75                  80

Gly Lys Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Ser Tyr Tyr Arg Ser Ala Trp Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
```

|     |     |     |     | 355 |     |     |     |     | 360 |     |     |     |     | 365 |     |
| --- | --- | --- | --- | --- | --- | --- | --- | --- | --- | --- | --- | --- | --- | --- | --- |

Val Tyr Thr Leu Pro Pro Ser Arg Asp Glu Leu Thr Lys Asn Gln Val
370                     375                     380

Ser Leu Thr Cys Leu Val Lys Gly Phe Tyr Pro Ser Asp Ile Ala Val
385                     390                     395                 400

Glu Trp Glu Ser Asn Gly Gln Pro Glu Asn Asn Tyr Lys Thr Thr Pro
                405                     410                     415

Pro Val Leu Asp Ser Asp Gly Ser Phe Phe Leu Tyr Ser Lys Leu Thr
                420                     425                     430

Val Asp Lys Ser Arg Trp Gln Gln Gly Asn Val Phe Ser Cys Ser Val
                435                     440                     445

Met His Glu Ala Leu His Asn His Tyr Thr Gln Lys Ser Leu Ser Leu
450                     455                     460

Ser Pro Gly Lys
465

<210> SEQ ID NO 23
<211> LENGTH: 1416
<212> TYPE: DNA
<213> ORGANISM: Artificial sequence
<220> FEATURE:
<223> OTHER INFORMATION: Synthetic oligonucleotide

<400> SEQUENCE: 23

```
gccgccacca tgggctggag ctggatcctg ctgttcctcc tgagcgtgac agcaggagtg      60
cacagccagg tccagctggt gcagagtggg cagaagtga agaaacccgg agcaagtgtc     120
aaagtgtcct gtaaggcaag cggatacgca ttttccaact tctggatgaa ttgggtgcgg     180
caggcaccag acagggcct ggagtggatg ggccagatct accctggcga cggcgatacc     240
aactataatg gcaagtttaa gggcagggtg accatgacac gcgacaccag catctccaca     300
gcctacatgg agctgtctcg gctgagaagc gacgatacag ccgtgtacta ttgcgccagg     360
tcttattatc gctctgcttg gttcgcctac tggggacagg gcactctggt caccgtctcc     420
tctgctagca ccaagggccc atcggtcttc cccctggcac cctcctccaa gagcacctct     480
gggggcacag cggccctggg ctgcctggtc aaggactact tccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg     780
ggaccgtcag tcttcctctt ccccccaaaa cccaaggaca cctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca agggcagccc cgagaaccca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
```
acgcagaaga gcctctcccc gtctccgggt aaatga 1416

<210> SEQ ID NO 24
<211> LENGTH: 468
<212> TYPE: PRT
<213> ORGANISM: Artificial sequence
<220> FEATURE:
<223> OTHER INFORMATION: Synthetic peptide

<400> SEQUENCE: 24

```
Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ala Phe
        35                  40                  45

Ser Asn Phe Trp Met Asn Trp Val Arg Gln Met Pro Gly Lys Gly Leu
    50                  55                  60

Glu Trp Met Gly Gln Ile Tyr Pro Gly Asp Gly Asp Thr Asn Tyr Asn
65                  70                  75                  80

Gly Lys Phe Lys Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Ser Tyr Arg Ser Ala Trp Phe Ala Tyr Trp
        115                 120                 125

Gly Gln Gly Thr Leu Val Thr Val Ser Leu Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
```

|  | 355 |  |  |  | 360 |  |  |  | 365 |  |  |
|---|---|---|---|---|---|---|---|---|---|---|---|

Val Tyr Thr Leu Pro Pro Ser Arg Asp Glu Leu Thr Lys Asn Gln Val
370 375 380

Ser Leu Thr Cys Leu Val Lys Gly Phe Tyr Pro Ser Asp Ile Ala Val
385 390 395 400

Glu Trp Glu Ser Asn Gly Gln Pro Glu Asn Asn Tyr Lys Thr Thr Pro
405 410 415

Pro Val Leu Asp Ser Asp Gly Ser Phe Phe Leu Tyr Ser Lys Leu Thr
420 425 430

Val Asp Lys Ser Arg Trp Gln Gln Gly Asn Val Phe Ser Cys Ser Val
435 440 445

Met His Glu Ala Leu His Asn His Tyr Thr Gln Lys Ser Leu Ser Leu
450 455 460

Ser Pro Gly Lys
465

<210> SEQ ID NO 25
<211> LENGTH: 1416
<212> TYPE: DNA
<213> ORGANISM: Artificial sequence
<220> FEATURE:
<223> OTHER INFORMATION: Synthetic oligonucleotide

<400> SEQUENCE: 25

| gccgccacca tgggctggag ctggatcctg ctgttcctcc tgagcgtgac agcaggagtg | 60 |
| cacagcgaag tgcagctggt gcagtctggc gctgaagtga agaaacctgg cgaaagcctg | 120 |
| aagattagtt gtaaagggtc tggatacgca ttcagcaact tctggatgaa ttgggtgcgg | 180 |
| cagatgccag gcaagggcct ggagtggatg ggacagatct accctggcga cggcgatacc | 240 |
| aactataatg gcaagtttaa gggccaggtg accatctccg ccgacaagtc tatcagcaca | 300 |
| gcctacctgc agtggagctc cctgaaggcc tccgatacag ccatgtacta ttgcgccaga | 360 |
| tcttactatc gctccgcttg gttcgcatac tgggggcagg gcactctggt caccgtgtca | 420 |
| ctggctagca ccaagggccc atcggtcttc cccctggcac cctcctccaa gagcacctct | 480 |
| gggggcacag cggccctggg ctgcctggtc aaggactact tccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gaaagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca cctcatgat ctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgtgtggt cagcgtcctc accgtcctgc accaggactg gctgaatggc | 1020 |
| aaggagtaca agtgcaaggt ctccaacaaa gccctcccag cccccatcga gaaaaccatc | 1080 |
| tccaaagcca agggcagccc cgagaaccac aggtgtaca ccctgccccc atcccgggat | 1140 |
| gagctgacca agaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 | acgcagaaga gcctctccct gtctccgggt aaatga                                    1416

<210> SEQ ID NO 26
<211> LENGTH: 233
<212> TYPE: PRT
<213> ORGANISM: Artificial sequence
<220> FEATURE:
<223> OTHER INFORMATION: Synthetic peptide

<400> SEQUENCE: 26

Met Gly Trp Ser Trp Ile Leu Leu Phe Leu Leu Ser Val Thr Ala Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Thr Ser Ile His Trp Tyr Gln Gln Lys Pro Asp Gln Ser Pro Lys
    50                  55                  60

Leu Leu Ile Lys Tyr Ala Ser Glu Ser Ile Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys Gln Gln Ser Asn Asn
            100                 105                 110

Trp Pro Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 27
<211> LENGTH: 711
<212> TYPE: DNA
<213> ORGANISM: Artificial sequence
<220> FEATURE:
<223> OTHER INFORMATION: Synthetic oligonucleotide

<400> SEQUENCE: 27
gccgccacca tgggctggag ctggatcctg ctgttcctcc tgagcgtgac agcaggagtg     60
cacagcgaga ttgtgctgac tcagagtcca gacttccagt cagtgacccc caaggagaaa    120
gtcaccatca catgccgggc aagccagtcc atcggcacaa gcattcactg gtaccagcag    180
aagcccgatc agtcccctaa gctgctgatc aaatatgcct ctgaaagtat ttcaggggtg    240
ccctctagat tcagcggctc cgggtctgga acagacttta ctctgaccat taactccctg    300
gaggctgaag atgccgctac ttactattgt cagcagagca taactggcc tctgacattc    360

```
gggcagggga ccaaagtgga aatcaaacga acgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g            711
```

```
<210> SEQ ID NO 28
<211> LENGTH: 468
<212> TYPE: PRT
<213> ORGANISM: Artificial sequence
<220> FEATURE:
<223> OTHER INFORMATION: Synthetic peptide

<400> SEQUENCE: 28
```

```
Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Thr Val Lys Ile Ser Cys Lys Val Ser Gly Tyr Ala Phe
        35                  40                  45

Ser Asn Phe Trp Met Asn Trp Val Gln Ala Pro Gly Lys Gly Leu
    50                  55                  60

Glu Trp Met Gly Gln Ile Tyr Pro Gly Asp Gly Asp Thr Asn Tyr Asn
65                  70                  75                  80

Gly Lys Phe Lys Gly Arg Val Thr Ile Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Ser Tyr Tyr Arg Ser Ala Trp Phe Ala Tyr Trp
        115                 120                 125

Gly Gln Gly Thr Leu Val Thr Val Ser Arg Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300
```

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 29
<211> LENGTH: 233
<212> TYPE: PRT
<213> ORGANISM: Artificial sequence
<220> FEATURE:
<223> OTHER INFORMATION: Synthetic peptide

<400> SEQUENCE: 29

Met Gly Trp Ser Trp Ile Leu Leu Phe Leu Leu Ser Val Thr Ala Gly
1               5                   10                  15

Val His Ser Glu Ile Val Met Thr Gln Ser Pro Ala Thr Leu Ser Val
            20                  25                  30

Ser Pro Gly Glu Arg Ala Thr Leu Ser Cys Arg Ala Ser Gln Ser Ile
        35                  40                  45

Gly Thr Ser Ile His Trp Tyr Gln Gln Lys Pro Gly Gln Ala Pro Arg
    50                  55                  60

Leu Leu Ile Tyr Tyr Ala Ser Glu Ser Ile Ser Gly Ile Pro Ala Arg
65                  70                  75                  80

Phe Ser Gly Ser Gly Ser Gly Thr Glu Phe Thr Leu Thr Ile Ser Ser
                85                  90                  95

Leu Gln Ser Glu Asp Phe Ala Val Tyr Tyr Cys Gln Gln Ser Asn Asn
            100                 105                 110

Trp Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 30
<211> LENGTH: 233
<212> TYPE: PRT
<213> ORGANISM: Artificial sequence
<220> FEATURE:
<223> OTHER INFORMATION: Synthetic peptide

<400> SEQUENCE: 30

Met Gly Trp Ser Trp Ile Leu Leu Phe Leu Leu Ser Val Thr Ala Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Ile
        35                  40                  45

Gly Thr Ser Ile His Trp Tyr Gln Gln Lys Pro Gly Gln Ala Pro Arg
    50                  55                  60

Leu Leu Ile Tyr Tyr Ala Ser Glu Ser Ile Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Ser Asn Asn
            100                 105                 110

Trp Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 31
<211> LENGTH: 233
<212> TYPE: PRT
<213> ORGANISM: Artificial sequence
<220> FEATURE:
<223> OTHER INFORMATION: Synthetic peptide

<400> SEQUENCE: 31

Met Gly Trp Ser Trp Ile Leu Leu Phe Leu Leu Ser Val Thr Ala Gly
1               5                   10                  15

Val His Ser Ala Ile Gln Leu Thr Gln Ser Pro Ser Ser Leu Ser Ala
            20                  25                  30

Ser Val Gly Asp Arg Val Thr Ile Thr Cys Arg Ala Ser Gln Ser Ile
            35                  40                  45

Gly Thr Ser Ile His Trp Tyr Gln Gln Lys Pro Gly Lys Ala Pro Lys
        50                  55                  60

Leu Leu Ile Tyr Tyr Ala Ser Glu Ser Ile Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Asn Asn
            100                 105                 110

Trp Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 32
<211> LENGTH: 233
<212> TYPE: PRT
<213> ORGANISM: Artificial sequence
<220> FEATURE:
<223> OTHER INFORMATION: Synthetic peptide

<400> SEQUENCE: 32

Met Gly Trp Ser Trp Ile Leu Leu Phe Leu Leu Ser Val Thr Ala Gly
1               5                   10                  15

Val His Ser Asp Ile Val Met Thr Gln Ser Pro Ser Leu Leu Ser Ala
            20                  25                  30

Ser Thr Gly Asp Arg Val Thr Ile Ser Cys Arg Ala Ser Gln Ser Ile
        35                  40                  45

Gly Thr Ser Ile His Trp Tyr Gln Gln Lys Pro Gly Lys Ala Pro Glu
    50                  55                  60

Leu Leu Ile Tyr Tyr Ala Ser Glu Ser Ile Ser Gly Val Pro Ser Arg
65                  70                  75                  80

Phe Ser Gly Ser Gly Ser Gly Thr Asp Phe Thr Leu Thr Ile Ser Cys
                85                  90                  95

Leu Gln Ser Glu Asp Phe Ala Thr Tyr Tyr Cys Gln Gln Ser Asn Asn
            100                 105                 110

Trp Pro Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

-continued

```
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 33
<211> LENGTH: 4
<212> TYPE: PRT
<213> ORGANISM: Artificial sequence
<220> FEATURE:
<223> OTHER INFORMATION: Synthetic peptide

<400> SEQUENCE: 33

Cys Gln Cys Arg
1

<210> SEQ ID NO 34
<211> LENGTH: 5
<212> TYPE: PRT
<213> ORGANISM: Artificial sequence
<220> FEATURE:
<223> OTHER INFORMATION: Synthetic peptide

<400> SEQUENCE: 34

Cys Gln Cys Arg Arg
1               5

<210> SEQ ID NO 35
<211> LENGTH: 6
<212> TYPE: PRT
<213> ORGANISM: Artificial sequence
<220> FEATURE:
<223> OTHER INFORMATION: Synthetic peptide

<400> SEQUENCE: 35

Cys Gln Cys Arg Arg Arg
1               5

<210> SEQ ID NO 36
<211> LENGTH: 7
<212> TYPE: PRT
<213> ORGANISM: Artificial sequence
<220> FEATURE:
<223> OTHER INFORMATION: Synthetic peptide

<400> SEQUENCE: 36

Cys Gln Cys Arg Arg Arg Arg
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic peptide

<400> SEQUENCE: 37

Cys Gln Cys Arg Arg Lys
1               5
```

```
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Cys Gln Cys Arg Arg Lys Asn
1               5

<210> SEQ ID NO 39
<211> LENGTH: 16
<212> TYPE: PRT
<213> ORGANISM: Artificial sequence
<220> FEATURE:
<223> OTHER INFORMATION: Synthetic peptide

<400> SEQUENCE: 39

Arg Arg Arg Arg Arg Arg Arg Arg Arg Cys Gln Cys Arg Arg Lys Asn
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Synthetic peptide

<400> SEQUENCE: 40

Gly Tyr Ala Phe Ser Asn Phe Trp Met Asn
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Synthetic peptide

<400> SEQUENCE: 41

Gln Ile Tyr Pro Gly Asp Gly Asp Thr Asn Tyr Asn Gly Lys Phe Lys
1               5                   10                  15

Gly

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Ser Tyr Tyr Arg Ser Ala Trp Phe Ala Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide

<400> SEQUENCE: 43
```

```
Arg Ala Ser Gln Ser Ile Gly Thr Ser Ile His
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Tyr Ala Ser Glu Ser Ile Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Gln Gln Ser Asn Asn Trp Pro Leu Thr
1               5
```

ANTIBODIES AGAINST THE MUC1-C/EXTRACELLULAR DOMAIN (MUC1-C/ECD)

This application claims benefit of priority to U.S. Provisional Application Ser. No. 62/371,320, filed Aug. 5, 2016, the entire contents of which are hereby incorporated by reference.

BACKGROUND

The sequence listing that is contained in the file named "GENUP0043US_ST25.txt", which is 56 KB (as measured in Microsoft Windows®) and was created on Jul. 27, 2017, is filed herewith by electronic submission and is incorporated by reference herein.

1. Field

The present disclosure relates generally to the fields of medicine, oncology and immunotherapeutics. More particularly, it concerns the development of immunoreagents for use in detecting and treating MUC1-positive cancers.

2. Background

Mucins are extensively O-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 1 (MUC1) can also signal to the interior of the cell through its cytoplasmic domain. MUC1 has no sequence similarity with other membrane-bound mucins, except for the presence of a sea urchin sperm protein-enterokinase-agrin (SEA) domain (Duraisamy et al., 2006). In that regard, MUC1 is translated as a single polypeptide and then undergoes autocleavage at the SEA domain Macao, 2006).

MUC1 has been studied extensively by the inventors and others for its role in cancer. As discussed above, human MUC1 is heterodimeric glycoprotein, translated as a single polypeptide and cleaved into N- and C-terminal subunits (MUC1-N and MUC1-C) in the endoplasmic reticulum (Ligtenberg et al., 1992; Macao et al., 2006; Levitin et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anti-cancer agents (Yin and Kufe, 2003; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 30, c-Src, protein kinase CS, and c-Abl (Raina et al., 2006; Li et al., 1998; Li et al., 2001; Ren et al., 2002). Inhibiting any of the foregoing interactions represents a potential point of therapeutic intervention for MUC1-related cancers.

SUMMARY

Thus, in accordance with the present disclosure, there is provided an antibody or an antigen-binding fragment thereof that binds selectively to a confirmational epitope from MUC1-C extracellular domain (MUC1-C/ECD) defined by SEQ ID NO: 1, wherein said antibody comprises a variable light domain sequence of SEQ ID NO: 2, and a variable heavy domain sequence of SEQ ID NO: 3, 4, 5 or 6. The antibody may be a single chain antibody, a single domain antibody, a chimeric antibody, or a Fab fragment thereof. The antibody may induce MUC-1-positive tumor cell death, such as through antibody-dependent cell cytotoxicity or complement-mediated cytoxocity.

The antibody may be a recombinant antibody having specificity for the confirmational epitope in MUC1-C/ECD and a distinct cancer cell surface antigen. The antibody may be an IgG. The antibody may further comprise a label, such as a peptide tag, an enzyme, a magnetic particle, a chromophore, a fluorescent molecule, a chemilluminescent molecule, or a dye. The antibody may further comprise an antitumor drug linked thereto, such as where the antitumor drug is linked to said antibody through a photolabile linker or through an enzymatically-cleaved linker. The antitumor drug may be a toxin, a radioisotope, a cytokine or an enzyme. The antibody may be conjugated to a nanoparticle or a liposome.

Also provided is a method of treating cancer comprising contacting a MUC1-positive cancer cell in a human subject with the antibody of claims 1-15, or an antigen-binding fragment thereof. The MUC1-positive cancer cell may be a solid tumor cell, such as a lung cancer cell, brain cancer cell, head & neck cancer cell, breast cancer cell, skin cancer cell, liver cancer cell, pancreatic cancer cell, stomach cancer cell, colon cancer cell, rectal cancer cell, uterine cancer cell, cervical cancer cell, ovarian cancer cell, testicular cancer cell, skin cancer cell, or esophageal cancer cell. The MUC1-positive cancer cell may be a leukemia or myeloma, such as where the leukemia or myeloma is acute myeloid leukemia, chronic myelogenous leukemia or multiple myeloma.

The method may further comprise contacting said MUC1-positive cancer cell with a second anti-cancer agent or treatment, such as from chemotherapy, radiotherapy, immunotherapy, hormonal therapy, or toxin therapy. The methods may also comprise a combination with surgery, such as where an unresectable cancer is rendered resectable. The second anti-cancer agent or treatment may inhibit an intracellular MUC1 function. The second anti-cancer agent or treatment may be given at the same time as said first agent, or given before and/or after said first agent. The MUC1-positive cancer cell may be a metastatic cancer cell, a multiply drug resistant cancer cell or a recurrent cancer cell. The treating may be through systemic administration, or administration local or regional to a tumor.

In addition, the disclosure provides a fusion protein comprising (i) an antibody that binds selectively to a confirmational epitope in MUC1-C extracellular domain (MUC1-C/ECD) defined by SEQ ID NO: 1, wherein said antibody comprises a variable light domain sequence of SEQ ID NO: 2, and a variable heavy domain sequence of SEQ ID NO: 3, 4, 5 or 6; and (ii) a second single chain antibody that binds to a T or B cell. The second single chain antibody may bind to CD3 or CD8. The second single chain antibody may bind to a T cell. The second single chain antibody may bind to a B cell. The fusion protein may further comprise a label or a therapeutic moiety.

In another embodiment, there is provided a chimeric antigen receptor comprising (i) an ectodomain comprising single chain antibody variable region that binds selectively to a confirmational epitope in MUC1-C/extracellular domain (MUC1-C/ECD) defined by SEQ ID NO: 1, wherein said antibody comprises a variable light domain sequence of SEQ ID NO: 2, and a variable heavy domain sequence of SEQ ID NO: 3, 4, 5 or 6, and with a flexible hinge attached at the C-terminus of said single chain antibody variable region; (ii) a transmembrane domain; and (iii) an endodomain, wherein said endodomain comprises a signal transduction function when said single-chain antibody variable region is engaged with MUC1. The transmembrande and/or endodomains may be derived from the same molecule, or the endodomain may comprise a CD3-zeta domain or a high affinity Fc∈RI. The flexible hinge may be from CD8α or Ig.

Other embodiments may include a cell expressing the antibody or antigen-binding fragment thereof as described above, a cell expressing the fusion protein as described above, a cell expressing the chimeric antigen receptor as described above.

Also provided are an isolated and purified nucleic acid encoding an antibody variable heavy domain selected from SEQ ID NO: 3, 4, 5 and 6, such as where the nucleic acid sequence is selected from SEQ ID NO: 8, 9, 10 and 11. Also provided are an isolated and purified nucleic acid encoding an antibody variable light domain of SEQ ID NO: 2, such as where the nucleic acid sequence is SEQ ID NO: 7. Also provided is a cell comprising the nucleic acids set forth above.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 8. FACS titration of 12 selected humanized antibodies for binding to HCT116/MUC1cells.

FIG. 9. Amino acid and nucleic acid sequences for VH1. Kozak sequence is in lower case, leader sequence is in italics, variable region is in bold, constant region is underlined, and stop codon is in normal text.

FIG. 10. Amino acid and nucleic acid sequences for VH2. Kozak sequence is in lower case, leader sequence is in italics, variable region is in bold, constant region is underlined, and stop codon is in normal text.

FIG. 11. Amino acid and nucleic acid sequences for VH3. Kozak sequence is in lower case, leader sequence is in italics, variable region is in bold, constant region is underlined, and stop codon is in normal text.

FIG. 12. Amino acid and nucleic acid sequences for VH5. Kozak sequence is in lower case, leader sequence is in italics, variable region is in bold, constant region is underlined, and stop codon is in normal text.

FIG. 13. Amino acid and nucleic acid sequences for VL1. Kozak sequence is in lower case, leader sequence is in italics, variable region is in bold, constant region is underlined, and stop codon is in normal text.

FIG. 14. Amino acid sequences for other chains. Leader sequence is in italics, variable region is in bold, constant region is underlined, and stop codon is in normal text.

DESCRIPTION OF ILLUSTRATIVE EMBODIMENTS

Figure 1:
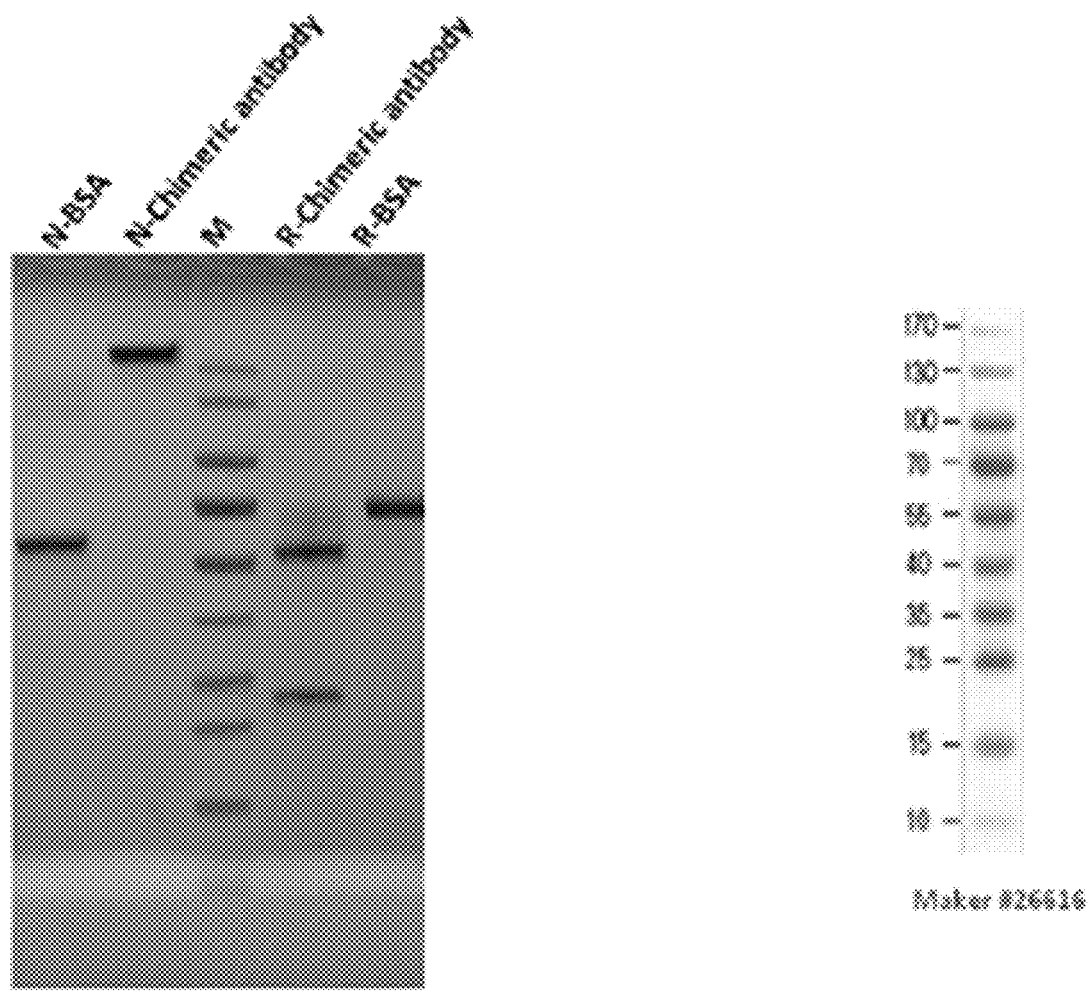
FIG. 1. Purity assessment of chimeric antibodybySDS-PAGE under reducing and non-reducing conditions. About 2 µg of protein was loaded in each lane. Lane M, page ruler pre-stained protein ladder (Thermo Scientific, Product No.: 26616).

The inventors have produced humanized antibodies against a 58 amino acid non-shed portion of the external domain of the MUC1-C protein. These antibodies have been demonstrated to bind selectively to this portion of MUC1-C, and as such, present an opportunity to block the activity of MUC1 following cleavage of the N-terminal region. They also can be used to deliver therapeutic payloads to MUC1-expressing cancer cells even following the cleavage of the N-terminal MUC1 domain. These and other aspects of the disclosure are described in greater detail below.

I. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72-amino acid cytoplasmic domain (CD) (Merlo et al., 1989). It is the 58 amino acid portion of the MUC1-C/ECD (italics) to which antibodies of the present disclosure bind. The human MUC1-C sequence is shown below:

(SEQ ID NO: 1)
*SVVVQLTLAFREGTINVHDVETQFNQYKTEAASRYNLTISDVSVSDVPFP*

*FSAQSGAGVPGWGIALLVLVCVLVALAIVYLIALAV*<u>CQCRRKNYGQLDIF</u>

PARDTYHPMSEYPTYHTHGRYVPPSSTDRSPYEKVSAGNGGSSLSYTNPA

VAATSANL

The bold sequence indicates the CD, and the underlined portion is an oligomer-inhibiting peptide. With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

B. Function

MUC1-C interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1-C is sufficient to induce anchorage-independent growth and tumorigenicity (Huang et al., 2003; Li et al., 2003b; Ren et al., 2002; Schroeder et al., 2004).

II. Producing Monoclonal Antibodies

A. General Methods

Antibodies to the MUC1-C/ECD may be produced by standard methods as are well known in the art (see, e.g., Antibodies: A Laboratory Manual, Cold Spring Harbor Laboratory, 1988; U.S. Pat. No. 4,196,265). The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this disclosure were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity to the confirmational epitope for MUC1-C/ECD, and in particular:

SVVVQLTLAFREGTINVHDVETQFNQYKTEAAS-RYNLTISDVSVSDVPFPFSAQSGAG (SEQ ID NO: 12). Those of skill in the art, by assessing the binding specificity/affinity of a given antibody using techniques well known to those of skill in the art, can determine whether such antibodies fall within the scope of the instant claims.

In on embodiment, the antibody is an Immunoglobulin G (IgG) antibody isotype. Representing approximately 75% of serum immunoglobulins in humans, IgG is the most abundant antibody isotype found in the circulation. IgG molecules are synthesized and secreted by plasma B cells. There are four IgG subclasses (IgG1, 2, 3, and 4) in humans, named in order of their abundance in serum (IgG1 being the most abundant). The range from having high to no affinity for the Fc receptor.

IgG is the main antibody isotype found in blood and extracellular fluid allowing it to control infection of body tissues. By binding many kinds of pathogens—representing viruses, bacteria, and fungi—IgG protects the body from infection. It does this via several immune mechanisms: IgG-mediated binding of pathogens causes their immobilization and binding together via agglutination; IgG coating of pathogen surfaces (known as opsonization) allows their recognition and ingestion by phagocytic immune cells; IgG activates the classical pathway of the complement system, a cascade of immune protein production that results in pathogen elimination; IgG also binds and neutralizes toxins. IgG also plays an important role in antibody-dependent cell-mediated cytotoxicity (ADCC) and intracellular antibody-mediated proteolysis, in which it binds to TRIM21 (the receptor with greatest affinity to IgG in humans) in order to direct marked virions to the proteasome in the cytosol. IgG is also associated with Type II and Type III Hypersensitivity. IgG antibodies are generated following class switching and maturation of the antibody response and thus participate predominantly in the secondary immune response. IgG is secreted as a monomer that is small in size allowing it to easily perfuse tissues. It is the only isotype that has receptors to facilitate passage through the human placenta. Along with IgA secreted in the breast milk, residual IgG absorbed through the placenta provides the neonate with humoral immunity before its own immune system develops. Colostrum contains a high percentage of IgG, especially bovine colostrum. In individuals with prior immunity to a pathogen, IgG appears about 24-48 hours after antigenic stimulation.

In another aspect, the antibodies may be defined by their variable sequences that determine their binding specificity. In all cases, the CDRs for the antibodies remain the same. The heavy chain CDRs are as follows: CDR1—GYAFSNFWMN (SEQ ID NO: 40); CDR2—QIYPGDGDTNYNGKFKG (SEQ ID NO: 41), CDR3—SYYRSAWFAY (SEQ ID NO: 42). The light chain CDRs are as follows: CDR1—RASQSIGTSIH (SEQ ID NO: 43); CDR2—YASESIS (SEQ ID NO: 44), CDR3—QQSNNWPLT (SEQ ID NO: 45). In addition, variable regions sequences are as follows:

Variable Heavy 1

(SEQ ID NO: 3)
QVQLVQSGAEVKKPGSSVKVSCKASGYAFSNFWMNWVRQAPGQGLEWMGQ
IYPGDGDTNYNGKFKGRVTITADKSTSTAYMELSSLRSEDTAVYYCARSY
YRSAWFAYWGQGTLVTVSS

Variable Heavy 1:

(SEQ ID NO: 8)
CAGGTGCAGCTGGTCCAGAGCGGGGCAGAAGTGAAAAAGCCAGGGTCAAG

TGTGAAGGTCTCATGTAAAGCAAGCGGATACGCATTTAGCAACTTCTGGA

TGAATTGGGTGAGGCAGGCACCAGGACAGGGCCTGGAGTGGATGGGCCAG

ATCTACCCTGGCGACGGCGATACCAACTATAATGGCAAGTTTAAGGGCCG

GGTGACCATCACAGCCGACAAGTCTACCAGCACAGCCTACATGGAGCTGA

GCTCCCTGCGGTCCGAGGATACAGCCGTGTACTATTGCGCCAGATCTTAT

TACAGATCAGCATGGTTCGCATACTGGGGCCAGGGGACACTGGTCACCGT

CTCATCC

Variable Heavy 2:

(SEQ ID NO: 4)
QVQLVQSGAEVKKPGASVKVSCKASGYAFSNFWMNWVRQAPGQGLEWMGQ
IYPGDGDTNYNGKFKGRVTMTRDTSTSTVYMELSSLRSEDTAVYYCARSY
YRSAWFAYWGQGTLVTVSS

Variable Heavy 2:

(SEQ ID NO: 9)
CAGGTCCAGCTGGTGCAGTCAGGAGCAGAAGTGAAAAAACCCGGCGCATC

AGTGAAAGTGTCTTGTAAAGCATCAGGCTACGCATTTAGCAACTTCTGGA

TGAATTGGGTGCGGCAGGCACCAGGACAGGGCCTGGAGTGGATGGGCCAG

ATCTACCCTGGCGACGGCGATACAAACTATAATGGCAAGTTTAAGGGCCG

GGTGACCATGACAAGAGACACCTCTACAAGCACCGTGTACATGGAGCTGA

GCTCCCTGAGGTCCGAGGATACCGCCGTGTACTATTGCGCCCGCTCTTAC

TATCGCTCCGCTTGGTTCGCTTATTGGGGACAGGGGACACTGGTCACCGT

CTCCTCA

Variable Heavy 3:

(SEQ ID NO: 5)
QVQLVQSGAEVKKPGASVKVSCKASGYAFSNFWMNWVRQAPGQGLEWMGQ
IYPGDGDTNYNGKFKGRVTMTRDTSISTAYMELSRLRSDDTAVYYCARSY
YRSAWFAYWGQGTLVTVSS

Variable Heavy 3:

(SEQ ID NO: 10)
CAGGTCCAGCTGGTGCAGAGTGGGGCAGAAGTGAAGAAACCCGGAGCAAG

TGTCAAAGTGTCCTGTAAGGCAAGCGGATACGCATTTTCCAACTTCTGGA

TGAATTGGGTGCGGCAGGCACCAGGACAGGGCCTGGAGTGGATGGGCCAG

ATCTACCCTGGCGACGGCGATACCAACTATAATGGCAAGTTTAAGGGCAG

GGTGACCATGACACGCGACACCAGCATCTCCACAGCCTACATGGAGCTGT

CTCGGCTGAGAAGCGACGATACAGCCGTGTACTATTGCGCCAGGTCTTAT

TATCGCTCTGCTTGGTTCGCCTACTGGGGACAGGGCACTCTGGTCACCGT

CTCCTCT

Variable Heavy 5:

(SEQ ID NO: 6)
EVQLVQSGAEVKKPGESLKISCKGSGYAFSNFWMNWVRQMPGKGLEWMGQ
IYPGDGDTNYNGKFKGQVTISADKSISTAYLQWSSLKASDTAMYYCARSY
YRSAWFAYWGQGTLVTVSL

Variable Heavy 5:

(SEQ ID NO: 11)
GAAGTGCAGCTGGTGCAGTCTGGCGCTGAAGTGAAGAAACCTGGCGAAAG

CCTGAAGATTAGTTGTAAAGGGTCTGGATACGCATTCAGCAACTTCTGGA

TGAATTGGGTGCGGCAGATGCCAGGCAAGGGCCTGGAGTGGATGGGACAG

ATCTACCCTGGCGACGGCGATACCAACTATAATGGCAAGTTTAAGGGCCA

GGTGACCATCTCCGCCGACAAGTCTATCAGCACAGCCTACCTGCAGTGGA

GCTCCCTGAAGGCCTCCGATACAGCCATGTACTATTGCGCCAGATCTTAC

TATCGCTCCGCTTGGTTCGCATACTGGGGCAGGGCACTCTGGTCACCGT

GTCACTG

Variable Light 1:
(SEQ ID NO: 2)
EIVLTQSPDFQSVTPKEKVTITCRASQSIGTSIHWYQQKPDQSPKLLIKY
ASESISGVPSRFSGSGSGTDFTLTINSLEAEDAATYYCQQSNNWPLTFGQ
GTKVEIK Variable Light 1:
(SEQ ID NO: 7)
GAGATTGTGCTGACTCAGAGTCCAGACTTCCAGTCAGTGACCCCCAAGGA
GAAAGTCACCATCACATGCCGGGCAAGCCAGTCCATCGGCACAAGCATTC
ACTGGTACCAGCAGAAGCCCGATCAGTCCCCTAAGCTGCTGATCAAATAT
GCCTCTGAAAGTATTTCAGGGGTGCCCTCTAGATTCAGCGGCTCCGGGTC
TGGAACAGACTTTACTCTGACCATTAACTCCCTGGAGGCTGAAGATGCCG
CTACTTACTATTGTCAGCAGAGCAATAACTGGCCTCTGACATTCGGGCAG
GGGACCAAAGTGGAAATCAAA Variable Heavy 4:
(SEQ ID NO: 17)
QVQLVQSGAEVKKPGATVKISCKVSGYAFSNFWMNWVQQAPGKGLEWMGQ
IYPGDGDTNYNGKFKGRVTITADTSTDTAYMELSSLRSEDTAVYYCARSY
YRSAWFAYWGQGTLVTVSR Variable Light 2:
(SEQ ID NO: 13)
EIVMTQSPATLSVSPGERATLSCRASQSIGTSIHWYQQKPGQAPRLLIYY
ASESISGIPARFSGSGSGTEFTLTISSLQSEDFAVYYCQQSNNWPLTFGG
GTKVEIK Variable Light 3:
(SEQ ID NO: 14)
EIVLTQSPATLSLSPGERATLSCRASQSIGTSIHWYQQKPGQAPRLLIYY
ASESISGIPARFSGSGSGTDFTLTISSLEPEDFAVYYCQQSNNWPLTFGG
GTKVEIK Variable Light 4:
(SEQ ID NO: 15)
AIQLTQSPSSLSASVGDRVTITCRASQSIGTSIHWYQQKPGKAPKLLIYY
ASESISGVPSRFSGSGSGTDFTLTISSLQPEDFATYYCQQSNNWPLTFGG
GTKVEIK Variable Light 5:
(SEQ ID NO: 16)
DIVMTQSPSLLSASTGDRVTISCRASQSIGTSIHWYQQKPGKAPELLIYY
ASESISGVPSRFSGSGSGTDFTLTISCLQSEDFATYYCQQSNNWPLTFGQ
GTKVEIK Specific examples with combinations of full variable sequences including framework regions are provided below:

TABLE 1

| Antibody Sequences | | |
|---|---|---|
| Antibody | Heavy Chain | Light Chain |
| VH1 + VL1 | SEQ ID NO: 3 | SEQ ID NO: 2 |
| VH2 + VL1 | SEQ ID NO: 4 | SEQ ID NO: 2 |
| VH3 + VL1 | SEQ ID NO: 5 | SEQ ID NO: 2 |
| VH5 + VL1 | SEQ ID NO: 6 | SEQ ID NO: 2 |
| VH1 + VL2 | SEQ ID NO: 3 | SEQ ID NO: 13 |
| VH1 + VL3 | SEQ ID NO: 3 | SEQ ID NO: 14 |
| VH1 + VL4 | SEQ ID NO: 3 | SEQ ID NO: 15 |
| VH1 + VL5 | SEQ ID NO: 3 | SEQ ID NO: 16 |
| VH2 + VL2 | SEQ ID NO: 4 | SEQ ID NO: 13 |
| VH2 + VL3 | SEQ ID NO: 4 | SEQ ID NO: 14 |
| VH2 + VL4 | SEQ ID NO: 4 | SEQ ID NO: 15 |
| VH2 + VL5 | SEQ ID NO: 4 | SEQ ID NO: 16 |
| VH3 + VL2 | SEQ ID NO: 5 | SEQ ID NO: 13 |
| VH3 + VL3 | SEQ ID NO: 5 | SEQ ID NO: 14 |
| VH3 + VL4 | SEQ ID NO: 5 | SEQ ID NO: 15 |
| VH3 + VL5 | SEQ ID NO: 5 | SEQ ID NO: 16 |
| VH4 + VL1 | SEQ ID NO: 17 | SEQ ID NO: 2 |
| VH4 + VL2 | SEQ ID NO: 17 | SEQ ID NO: 13 |
| VH4 + VL3 | SEQ ID NO: 17 | SEQ ID NO: 14 |
| VH4 + VL4 | SEQ ID NO: 17 | SEQ ID NO: 15 |
| VH4 + VL5 | SEQ ID NO: 17 | SEQ ID NO: 16 |
| VH5 + VL2 | SEQ ID NO: 6 | SEQ ID NO: 13 |
| VH5 + VL3 | SEQ ID NO: 6 | SEQ ID NO: 14 |
| VH5 + VL4 | SEQ ID NO: 6 | SEQ ID NO: 15 |
| VH5 + VL5 | SEQ ID NO: 6 | SEQ ID NO: 16 |

Furthermore, the antibodies sequences may vary from the sequences provided above, optionally using methods discussed in greater detail below. For example, amino sequences may vary from those set out above in that (a) the variable regions may be segregated away from the constant domains of the light chains, (b) the amino acids may vary from those set out above while not drastically affecting the chemical properties of the residues thereby (so-called conservative substitutions), (c) the amino acids may vary from those set out above by a given percentage, e.g., 80%, 85%, 90%, 91%, 92%, 93%, 94%, 95%, 96%, 97%, 98% or 99% homology. Alternatively, the nucleic acids encoding the antibodies may (a) be segregated away from the constant domains of the light chains, (b) vary from those set out above while not changing the residues coded thereby, (c) may vary from those set out above by a given percentage, e.g., 70%, 75%, 80%, 85%, 90%, 91%, 92%, 93%, 94%, 95%, 96%, 97%, 98% or 99% homology, or (d) vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C.

In making conservative changes in amino acid sequence, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

C. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). In particular, IgM antibodies may be converted to IgG antibodies. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies can be generated by subcloning heavy and light chain Fv DNAs from the cloning vector into a Lonza pConIgG1 or pConK2 plasmid vector, transfected into 293 Freestyle cells or Lonza CHO cells, and collected and purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In one embodiment, has been modified to attenuate immune reaction when used in human therapy. Such "humanized antibodies" may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

The present disclosure also contemplates isotype modification. By modifying the Fc region to have a different isotype, different functionalities can be achieved. For example, changing to IgG4 can reduce immune effector functions associated with other isotypes.

Modified antibodies may be made by any technique known to those of skill in the art, including expression through standard molecular biological techniques, or the chemical synthesis of polypeptides. Methods for recombinant expression are addressed elsewhere in this document.

D. Expression

Nucleic acids according to the present disclosure will encode antibodies, optionally linked to other protein sequences. As used in this application, the term "a nucleic acid encoding a MUC1-C antibody" refers to a nucleic acid molecule that has been isolated free of total cellular nucleic acid. In certain embodiments, the disclosure concerns antibodies that are encoded by any of the sequences set forth herein.

TABLE 2

| CODONS | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |

TABLE 2-continued

CODONS

| Amino Acids | | | Codons |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The DNA segments of the present disclosure include those encoding biologically functional equivalent proteins and peptides of the sequences described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Within certain embodiments, expression vectors are employed to express a MUC1-C ligand trap in order to produce and isolate the polypeptide expressed therefrom. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment.

A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively direct the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 3 lists several elements/promoters that may be employed, in the context of the present disclosure, to regulate the expression of a gene. This list is not intended to be exhaustive of all the possible elements involved in the promotion of expression but, merely, to be exemplary thereof. Table 4 provides examples of inducible elements, which are regions of a nucleic acid sequence that can be activated in response to a specific stimulus.

TABLE 3

| Promoter and/or Enhancer | |
| --- | --- |
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; |

TABLE 3-continued

Promoter and/or Enhancer

| Promoter/Enhancer | References |
|---|---|
| | Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI) × poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present disclosure. Some such promoters are set forth in Table 5.

TABLE 5

TUMOR SPECIFIC PROMOTERS

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas cells | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |

TABLE 5-continued

TUMOR SPECIFIC PROMOTERS

| Tissue-specific promoter | Cancers in which promoter is active | Normal cells in which promoter is active |
|---|---|---|
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

2. IRES

In certain embodiments of the disclosure, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference).

5. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher's disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors. In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present disclosure comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a $\psi$ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The $\psi$ sequence is required for the packaging of the adenoviral genome. A common approach for generating adenoviruses for use as a gene transfer vectors is the deletion of the E1 gene (E1−), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1−, replication-deficient virus is then proliferated in a "helper" cell line that provides the E1 polypeptides in trans (e.g., the human embryonic kidney cell line 293). Thus, in the present disclosure it may be convenient to introduce the transforming construct at the position from which the E1-coding sequences have been removed. However, the position of insertion of the construct within the adenovirus sequences is not critical to the disclosure. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; and 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1996) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the disclosure. The adenovirus may be of any of the 42 different known serotypes and/or subgroups A-F. Adenovirus type 5 of subgroup C is the preferred starting material in order to obtain the conditional replication-defective adenovirus vector for use in the present disclosure. This is because adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Adenovirus growth and manipulation is known to those of skill in the art, and exhibits broad host range in vitro and in vivo (U.S. Pat. Nos. 5,670,488; 5,932,210; and 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors. In certain embodiments of the disclosure, the uses of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present disclosure may be genetically modified in such a way that some of the structural, infectious genes of the native virus have been removed and replaced instead with a nucleic acid sequence to be delivered to a target cell (U.S. Pat. Nos. 5,858,744; and 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present disclosure are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; and 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present disclosure (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery include a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado and Chen, 1999; Engel and Kohn, 1999), cancer (Clay et al., 1999), cerebrovascular disease (Weihl et al., 1999) and hemophilia (Kay, 1998).

Herpesviral Vectors. Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or α genes, Early (E) or β genes and Late (L) or γ genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; and 5,851,826, each specifically incorporated herein by reference in its entirety). One IE protein, ICP4, also known as α4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors. Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif vpr, vpu and nefare deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-lac gene in this disclosure, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present disclosure, one may graft or transplant cells infected with the recombinant lentivirus ex vivo, or infect cells in vivo.

Other Viral Vectors. The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

In certain embodiments, vaccinia viral vectors are contemplated for use in the present disclosure. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., $P_{450}$ (U.S. Pat. No. 5,506,138). The preparation, growth and manipulation of vaccinia viruses are described in U.S. Pat. Nos. 5,849,304 and 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA.

Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors. Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

10. Non-Viral Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection. In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present disclosure include the introduction of a nucleic acid by direct microinjection. Direct microinjection has been used to introduce nucleic acid constructs into Xenopus oocytes (Harland and Weintraub, 1985).

Electroporation. In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human κ-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 92/17598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate. In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading. Additional embodiments of the present disclosure include the introduction of a nucleic acid by direct sonic loading. LTK⁻ fibroblasts have been transfected with the thymidine kinase gene by sonication loading (Fechheimer et al., 1987).

Liposome-Mediated Transfection. In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor-Mediated Transfection. Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner.

11. Expression Systems

Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MaxBac® 2.0 from Invitrogen® and BacPack™ Baculovirus Expression System From Clontech®. Other examples of expression systems include Stratagene®'s Complete Control™ Inducible Mammalian Expression System, which involves a synthetic ecdysone-inducible receptor, or its pET Expression System, an *E. coli* expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr that confers resistance to; gpt, that confers resistance to mycophenolic acid; neo, that confers resistance to the aminoglycoside G418; and hygro, that confers resistance to hygromycin.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

F. Single Chain/Single Domain Antibodies

A Single Chain Variable Fragment (scFv) is a fusion of the variable regions of the heavy and light chains of immunoglobulins, linked together with a short (usually serine, glycine) linker. This chimeric molecule, also known as a single domain antibody, retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single domain or single chain variable fragments lack the constant Fc region found in complete antibody molecules, and thus, the common binding sites (e.g., protein A/G) used to purify antibodies (single chain antibodies include the Fc region). These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

G. Modified Antibodies

1. CARs

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of cancer-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signalling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However the best spacer often has to be determined empirically.

Transmembrane Domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed. For example, chimeric CD28 and OX40 can be used with CD3-Zeta to transmit a proliferative/survival signal, or all three can be used together.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

Adoptive transfer of T cells expressing chimeric antigen receptors is a promising anti-cancer therapeutic as CAR-modified T cells can be engineered to target virtually any tumor associated antigen. There is great potential for this approach to improve patient-specific cancer therapy in a profound way. Following the collection of a patient's T cells, the cells are genetically engineered to express CARs specifically directed towards antigens on the patient's tumor cells, then infused back into the patient. Although adoptive transfer of CAR-modified T-cells is a unique and promising cancer therapeutic, there are significant safety concerns. Clinical trials of this therapy have revealed potential toxic effects of these CARs when healthy tissues express the same target antigens as the tumor cells, leading to outcomes similar to graft-versus-host disease (GVHD). A potential solution to this problem is engineering a suicide gene into the modified T cells. In this way, administration of a prodrug designed to activate the suicide gene during GVHD triggers apoptosis in the suicide gene-activated CAR T cells. This method has been used safely and effectively in hematopoietic stem cell transplantation (HSCT). Adoption of suicide gene therapy to the clinical application of CAR-modified T cell adoptive cell transfer has potential to alleviate GVHD while improving overall anti-tumor efficacy.

2. ADCs

Antibody Drug Conjugates or ADCs are a new class of highly potent biopharmaceutical drugs designed as a targeted therapy for the treatment of people with cancer. ADCs are complex molecules composed of an antibody (a whole mAb or an antibody fragment such as a single-chain variable fragment, or scFv) linked, via a stable chemical linker with labile bonds, to a biological active cytotoxic (anticancer) payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional chemotherapeutic agents, antibody-drug conjugates target and attack the cancer cell so that healthy cells are less severely affected.

In the development ADC-based anti-tumor therapies, an anticancer drug (e.g., a cell toxin or cytotoxin) is coupled to an antibody that specifically targets a certain tumor marker (e.g., a protein that, ideally, is only to be found in or on tumor cells; in this case MUC1). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents.

A stable link between the antibody and cytotoxic (anticancer) agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic (anti-cancer) agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the cancer cell where it releases the cytotoxic agent. The difference is that the cytotoxic payload delivered via a cleavable linker can escape from the targeted cell and, in a process called "bystander killing," attack neighboring cancer cells.

Another type of cleavable linker, currently in development, adds an extra molecule between the cytotoxic drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

3. BitES or Bi-Specific Antibodies

Bi-specific T-cell engagers (BiTEs) are a class of artificial bispecific monoclonal antibodies that are investigated for the use as anti-cancer drugs. They direct a host's immune system, more specifically the T cells' cytotoxic activity, against cancer cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule, in this case MUC1.

Like other bispecific antibodies, and unlike ordinary monoclonal antibodies, BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

BiTEs that were in clinical trials as of July 2010 include Blinatumomab (MT103) for the treatment of non-Hodgkin's lymphoma and acute lymphoblastic leukemia, directed towards CD19, a surface molecule expressed on B cells; and MT110 for the treatment of gastrointestinal and lung cancers, directed towards the EpCAM antigen.

Utilizing the same technology, melanoma (with MCSP specific BiTEs) and acute myeloid leukemia (with CD33 specific BiTEs) can be targeted. Research in this area is currently ongoing. Another avenue for novel anti-cancer therapies is re-engineering some of the currently used conventional antibodies like trastuzumab (targeting HER2/neu), cetuximab and panitumumab (both targeting the EGF receptor), using the BiTE approach. BiTEs against CD66e and EphA2 are being developed as well.

III. Pharmaceutical Formulations and Treatment of Cancer

A. Cancers

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Cancer cells to which the methods of the present disclosure can be applied include generally any cell that expresses MUC1, and more particularly, that overexpresses MUC1. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present disclosure may be particularly applied to such cancers so as to render them resectable, to prolong or re-induce remission, to inhibit angiogenesis, to prevent or limit metastasis, and/or to treat multi-drug resistant cancers. At a cellular level, this may translate into killing cancer cells, inhibiting cancer cell growth, or otherwise reversing or reducing the malignant phenotype of tumor cells.

B. Formulation and Administration

The present disclosure provides pharmaceutical compositions comprising anti-MUC1-C antibodies. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The antibodies of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or admininstration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

C. Combination Therapies

In the context of the present disclosure, it also is contemplated that anti-MUC1-C antibodies described herein could be used similarly in conjunction with chemo- or radiotherapeutic intervention, or other treatments. It also may prove effective, in particular, to combine anti-MUC1-C/ECD antibodies with other therapies that target different aspects of MUC1 function, such as peptides and small molecules that target the MUC1 cytoplasmic domain.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with an anti-MUC1-C antibody according to the present disclosure and at least one other agent. These compositions would be provided in a combined amount effective to kill or inhibit proliferation of the cell. This process may involve contacting the cells with the anti-MUC1-C antibody according to the present disclosure and the other agent(s) or factor(s) at the same time. This may be achieved by contacting the cell with a single composition or pharmacological formulation that includes both agents, or by contacting the cell with two distinct compositions or formulations, at the same time, wherein one composition includes the anti-MUC1-C antibody according to the present disclosure and the other includes the other agent.

Alternatively, the anti-MUC1-C antibody therapy may precede or follow the other agent treatment by intervals ranging from minutes to weeks. In embodiments where the other agent and the anti-MUC1 antibody are applied separately to the cell, one would generally ensure that a significant period of time did not expire between each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either anti-MUC1 antibody or the other agent will be desired. Various combinations may be employed, where an anti-MUC1-C antibody according to the present disclosure therapy is "A" and the other therapy is "B", as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. Again, to achieve cell killing, both agents are delivered to a cell in a combined amount effective to kill the cell.

Agents or factors suitable for cancer therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," may be used. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with the present disclosure. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, and mitomycin C. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in cancer therapy in accordance with the present disclosure.

Another possible therapy is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, it also is contemplated that immunotherapy, hormone therapy, toxin therapy and surgery can be used. In particular, one may employ targeted therapies such as Avastin, Erbitux, Gleevec, Herceptin and Rituxan.

One particularly advantageous approach to combination therapy is to select a second agent that targets MUC1. In copending application filed by the present inventors, there are disclosed methods of inhibiting a MUC1-positive tumor cell in a subject comprising administering to said subject a MUC1 peptide of at least 4 consecutive MUC1 residues and no more than 20 consecutive MUC1 residues and comprising the sequence CQC, wherein the amino-terminal cysteine of CQC is covered on its NH$_2$-terminus by at least one amino acid residue that need not correspond to the native MUC-1 transmembrane sequence. The peptide may comprise at least 5 consecutive MUC1 residues, at least 6 consecutive MUC1 residues, at least 7 consecutive MUC1 residues, at least 8 consecutive MUC1 residues and the sequence may more specifically comprise CQCR (SEQ ID NO: 33), CQCRR (SEQ ID NO: 34), CQCRRR (SEQ ID NO: 35), CQCRRRR (SEQ ID NO: 36), CQCRRK (SEQ ID NO: 37), CQCRRKN (SEQ ID NO: 38), or RRRRRRRRRCQCRRKN (SEQ ID NO: 39). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K. The peptide may comprise all L amino acids, all D amino acids, or a mix of L and D amino acids. See U.S. Pat. No. 8,524,669.

A variation on this technology is described in U.S. patent application Ser. No. 13/026,858. In that application, methods of inhibiting a MUC1-positive cancer cell are disclosed comprising contacting the cell with a MUC1 peptide of at least 4 consecutive MUC1 residues and no more than 20 consecutive MUC1 residues and comprising the sequence CQC, wherein (i) the amino-terminal cysteine of CQC is covered on its NH$_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The MUC1-positive cell may be a solid tumor cell, such as a lung cancer cell, a brain cancer cell, a head & neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a skin cancer cell or a esophageal cancer cell. The MUC1-positive cell may be a leukemia or myeloma cell, such as acute myeloid leukemia, chronic myelogenous leukemia or multiple myeloma. The peptide may be a stapled peptide, a cyclized peptide, a peptidomimetic or peptoid. The method may further comprise contacting the cell with a second anti-cancer agent, such as where the second anti-cancer agent is contacted prior to the peptide, after the peptide or at the same time as the peptide. Inhibiting may comprise inhibiting cancer cell growth, cancer cell proliferation or inducing cancer cell death, such as by apoptosis.

Another technology advanced by the inventors (see U.S. patent application Ser. No. 13/045,033) involves methods of inhibiting inflammatory signaling in a cell comprising contacting said cell with a flavone having the structure of:
[INSERT]
or a salt thereof, wherein:
- $R_1$ is H, —OH, =O, substituted or unsubstituted alkyl ($C_{1-8}$), alkoxy($C_{1-8}$), haloalkyl($C_{1-8}$), substituted phenyl or unsubstituted phenyl, wherein if $R_1$ is =O, $C_7$-$C_8$ is a double bond;
- $R_2$ is H, —OH, alkyl($C_{1-8}$), substituted phenyl, unsubstituted phenyl, phenyl, phenyl thiazole, imidazole, pyrazole or furan;
- $R_3$ is H, —OH, =O, halogen, haloalkyl($C_{1-8}$), substituted or unsubstituted alkyl($C_{1-8}$), substituted phenyl or unsubstituted phenyl, wherein if $R_3$ is =O, $C_8$-$C_9$ is a double bond;
- $R_4$ is H or —OH;
- $R_5$ is H, —OH, substituted or unsubstituted alkyl($C_{1-8}$) or alkoxy($C_{1-8}$), or $OR_8$, wherein $R_8$ is alkyl($C_{1-8}$), an ester or an amide;
- $R_6$ is H, —OH, substituted or unsubstituted alkyl($C_{1-8}$) or alkoxy($C_{1-8}$), or $OR_8$, wherein $R_8$ is alkyl($C_{1-8}$), an ester or an amide; and
- $R_7$ is H, —OH, or substituted or unsubstituted alkyl($C_{1-8}$), with the proviso that $R_1$ and $R_3$ cannot both be =O. $R_1$ may be =O. $R_3$ may be =O. The flavone in Morin, Apigenin, Kaempferol, Fisetin, PD98059, 7-(benzyloxy)-4-(trifluoromethyl)-2H-chromen-2-one or 7-[(3-oxobutan-2-yl)oxy]-4-phenyl-2H-chromen-2-one, or a salt of any of the foregoing.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. Antibody Conjugates

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups are often used to bind radioisotopes to antibody and exist as metallic ions are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, there are immunodetection methods for binding, purifying, removing, quantifying and otherwise generally detecting MUC1 and its associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of MUC1-C antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to MUC1 present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the MUC1 is added to the wells. After binding and washing to remove non-specifically bound immune complexes, the bound antigen may be detected. Detection may be achieved by the addition of another anti-MUC1-C antibody that is linked to a detectable label. This type of ELISA is a simple "sandwich ELISA." Detection may also be achieved by the addition of a second anti-MUC1-C antibody, followed by the addition of a third antibody that has binding affinity for the second antibody, with the third antibody being linked to a detectable label.

In another exemplary ELISA, the samples suspected of containing the MUC1 antigen are immobilized onto the well surface and then contacted with anti-MUC1-C antibody. After binding and washing to remove non-specifically bound immune complexes, the bound anti-MUC1-C antibodies are detected. Where the initial anti-MUC1-C antibodies are linked to a detectable label, the immune complexes may be detected directly. Again, the immune complexes may be detected using a second antibody that has binding affinity for the first anti-MUC1-C antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PB S)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, there are immunodetection kits for use with the immunodetection methods described above. The immunodetection kits will thus comprise, in suitable container means, a first antibody that binds to MUC1 antigen, and optionally an immunodetection reagent.

In certain embodiments, the MUC1-C antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the MUC1 antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VI. Examples

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Antibody Humanization

Objective. The aim of this project is to humanize a mouse monoclonal antibody (mAb) provided by client using CDR grafting method. Briefly, five (5) light chain and five (5) heavy chain variable domain human acceptors were selected based on their homologies with mouse antibody. The sequences of five (5) humanized VLs and five (5) humanized VHs were obtained after directly grafting the CDRs of mouse antibody to the human acceptor frameworks. Meantime, N-glycosylation motifs were analyzed. Potential glycosylation sites in the candidate human variable regions should therefore be avoided.

Materials. Amino acid sequences of a mouse monoclonal antibody provided the basis for alignment with human acceptor sequences.

Humanization Design. The variable domain sequences of the mouse monoclonal antibody were searched against the human IgG germline database. Five human framework sequences with high homology were chosen as human acceptors for both light and heavy chains. The humanized variable domains of five (5) light chains were denoted as VL1, VL2, VL3, VL4 and VL5, while the humanized variable domains of five (5) heavy chains were denoted as VH1, VH2, VH3, VH4 and VH5.

Example 2

Chimeric Antibody Production

Project Overview. This project aimed to humanize a mouse monoclonal antibody (mAb) provided by client using CDR grafting method. Briefly, five heavy chain and five light chain human acceptors were selected for CDR grafting based on their homologies with the parental mouse mAb. Then twenty-five humanized antibodies were expressed in HEK293 cells and their affinity was analyzed by affinity ranking and FACS titration.

Antibody Humanization by CDR Grafting: Selection of Acceptor Frameworks. The variable domain sequences of parental antibody were searched in the database of human germline using NCBI Ig-Blast (world-wide-web at ncbi.nlm.nih.gov/projects/igblast/). Five human acceptors (i.e. human variable domains with high homology to the parental antibody) for both heavy chain and light chain were selected. The CDRs of human acceptors were replaced with their mouse counterparts, resulting in humanized antibody variable sequences. The humanized variable domains of heavy chains were named VH1, VH2, VH3, VH4 and VH5; while the humanized variable domains of light chains were named VL1, VL2, VL3, VL4 and VL5. The full sequences of humanized heavy and light chains are shown in Appendix I.

Construction and Production of Chimeric Antibody and Humanized Antibodies. The DNA sequences encoding the parental mouse mAb and the humanized heavy and light chains were synthesized and inserted intopTGE5 vector to construct IgG expressing vectors for expression of chimericantibody and humanized antibodies in mammalian cells. Antibody expression was conducted in 100 ml HEK293 cell culture and the supernatants were purified with protein A affinity column. The concentration and purity of proteins were assessed by $OD_{280}$ and SDS-PAGE, respectively.

ELISA Titration. A microtiter plate was coated with antigen protein (1 µg/ml) in 100 µl coating buffer at 4° C. overnight, and subsequently incubated with blocking buffer at 37° C. for 2 hours. The plate was washed with washing buffer and incubated with 100 µl chimeric or humanized antibody at a series of concentrations at 37° C. for 1.5 hours. The ELISA plate was then washed with washing buffer and incubated with 100 µl secondary antibody (0.1 µg/ml goat anti-human IgG [HRP]) for 45 minutes. After washing, the reaction was developed with 100 µl TMB substrate for 10 minutes at room temperature. The reaction was stopped by adding 100 µl of 1 M HCl. The absorbance values were measured at 450 nm using a spectrometer.

FACS Titration. To assess cell binding, $2 \times 10^5$ HCT116/MUC1 cells per well were washed with PBS twice and incubated in 200 µl of serial dilutions of chimeric or humanized antibodies for 1 hour at room temperature. After washing 3 times with PBS, secondary antibody (2 µg/ml Alexa Flour®488 goat anti-human IgG) was added to cells and incubated for 30 minutes at room temperature. After washing with PBS, cells were analyzed by using FACSCalibur (BD Bioscience, San Jose, Calif.) and Flowjo software.

Affinity Measurement and Affinity Ranking by Biacore T200. Antibody affinity was determined using a Surface Plasmon Resonance (SPR) biosensor, Biacore T200 (GE Healthcare). Antibody was immobilized on the sensor chip through Fc capture method. Antigen protein was used as the analyte. The data of dissociation (kd) and association (ka) rate constants were obtained using Biacore T200 evaluation software. The apparent equilibrium dissociation constants (KD) were calculated from the ratio of kd over ka. For affinity ranking, twenty-five humanized antibodies plus chimericantibody were injected and captured on sensor chip individually. The antibodies were ranked based on their dissociation rates (kd).

Chimeric Antibody Production. Parental chimeric antibody was expressed and purified according to GenScript's SOP. The purified IgG migrated as ~170 kDa band in SDS-PAGE under non-reducing condition, ~55 kDa and ~30 kDa bands under reducing condition. The purity of IgG is >90% evaluated based on the SDS-PAGE result (FIG. 1). The yield of the purified IgG expressed in 100 ml cell culture was 0.53 mg.

Figure 2:
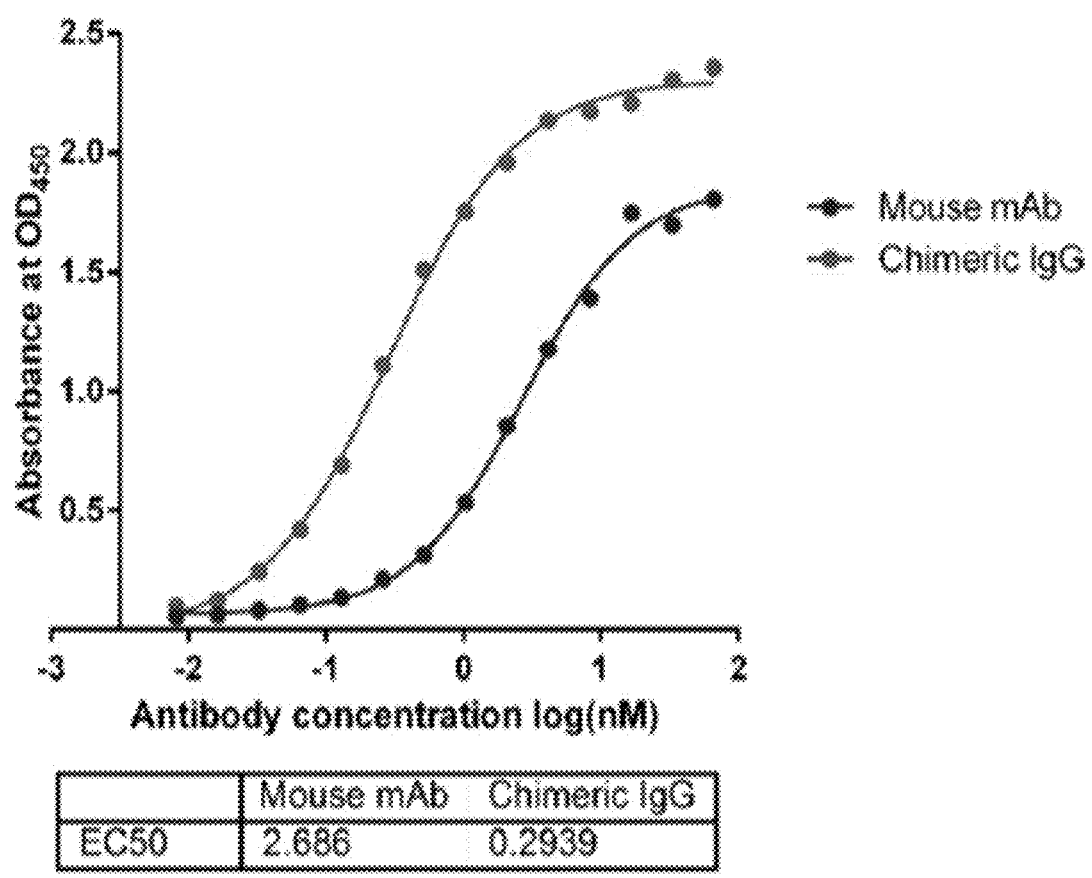
FIG. 2. Validation of antigen and chimeric antibody interactionby ELISA titration. MuC1-SEA-His protein was coated on ELISA plate at 1 µg/ml. Goat anti-human IgG and goat anti-mouse IgG were used as secondary antibodies at 0.1 µg/ml.

Chimeric Antibody Binding Confirmation. The ELISA result indicated the half maximal effective concentration ($EC_{50}$) of the chimeric antibody was at 0.29 nM, while the moue mAb was at 2.69 nM as shown in FIG. 2.

Figure 3:
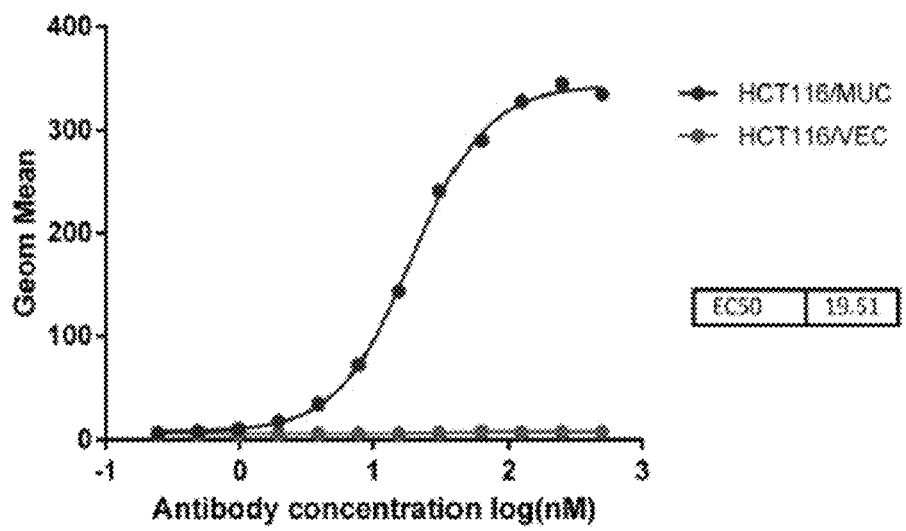
FIG. 3. FACS titration of chimeric antibody for binding to HCT116/MUC1 cells. HCT116/MUC1 was MUC1 overexpressed cell line and HCT116/Vector was negative control cell line without MUC1 expression.

HCT116/MUC1 (MUC1 overexpressed cell line) and HCT116/Vector (negative control cell line) were used to evaluate binding specificity and potency of the chimeric antibody by FACS titration. It showed that chimeric antibody could bind HCT116/MUC1 cells with $EC_{50}$ at 19.51 nM and did not bind HCT116/Vector cells as shown in FIG. 3.

Figure 4:
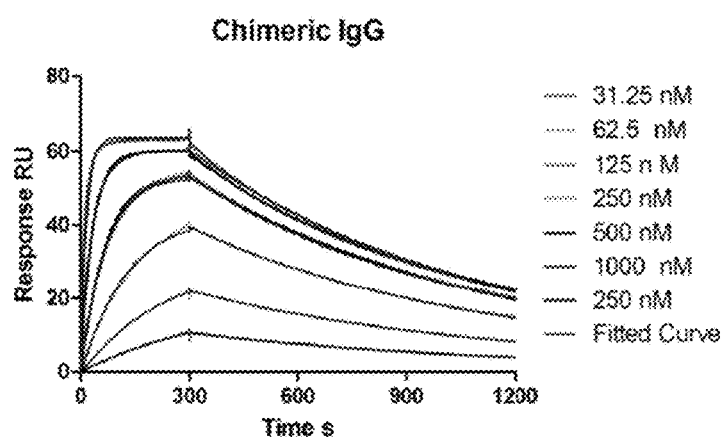
FIG. 4. Affinity measurement of chimericantibody. Real-time responses were shown with colored curves. Fitting of Biacore experimental data to 1:1 interaction model was shown in black. The antigen concentrations were at 31.25 nM, 62.5 nM, 125 nM, 250 nM (×2), 500 nM, and 1000 nM in use, respectively.

The affinity of chimeric IgG antibody with MUC1-SEA-His protein was 18 nM measured by Biacore T200 as shown in FIG. 4.

Figure 5:
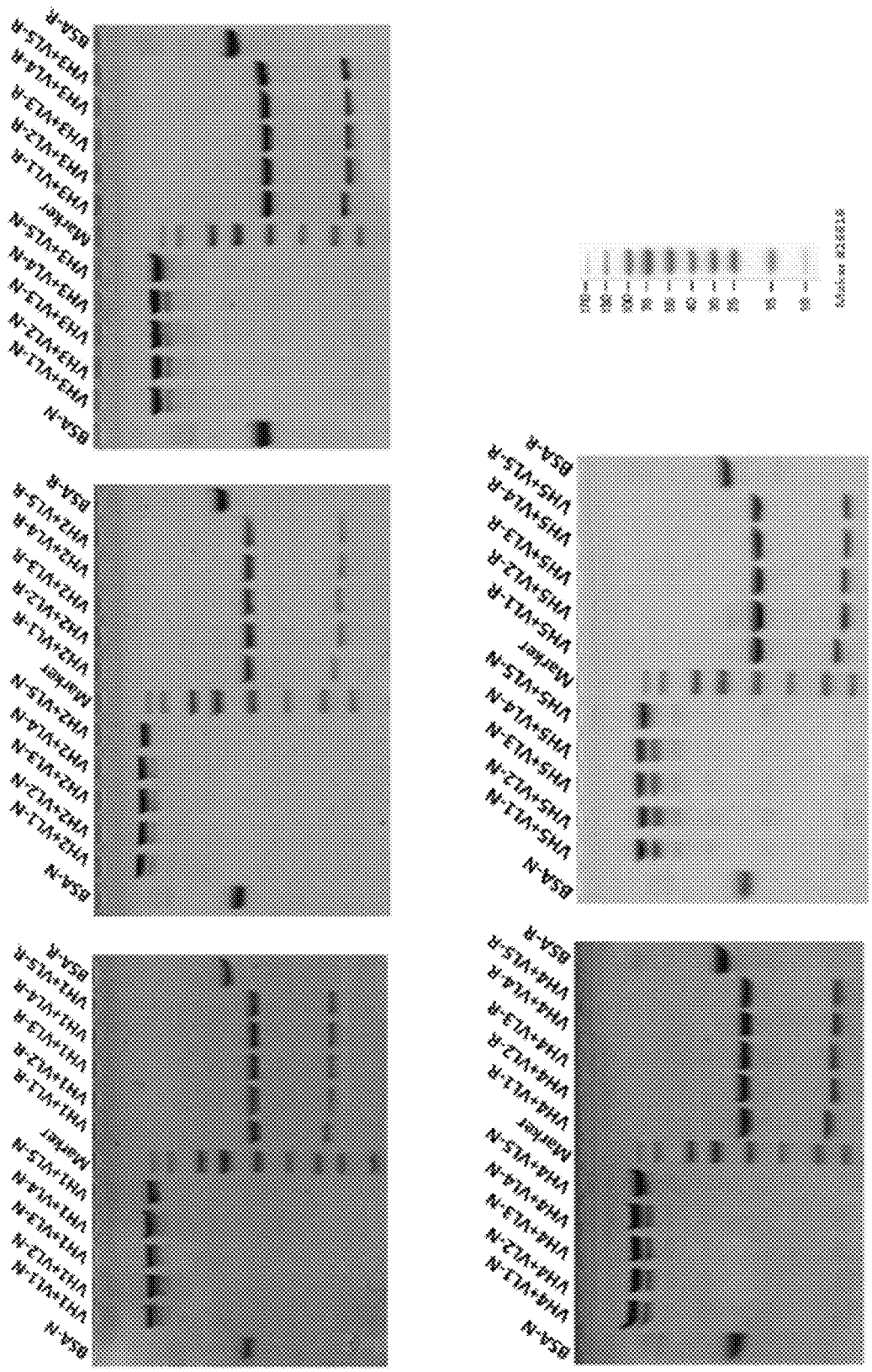
FIG. 5. Purity assessment of twenty-five humanized antibodies by SDS-PAGE under reducing and non-reducing conditions. About 2 µg of protein was loaded in each lane. Lane Marker, page ruler pre-stained protein ladder (Thermo Scientific, Product No. 26616).

Twenty-five humanized antibodies were expressed in 100 ml HEK293cells and purified by protein A resin. The purity of IgGs was over 90% as evaluated by SDS-PAGE (FIG. 5). The yields of purified IgGs were listed in Table 1.

Figure 6:
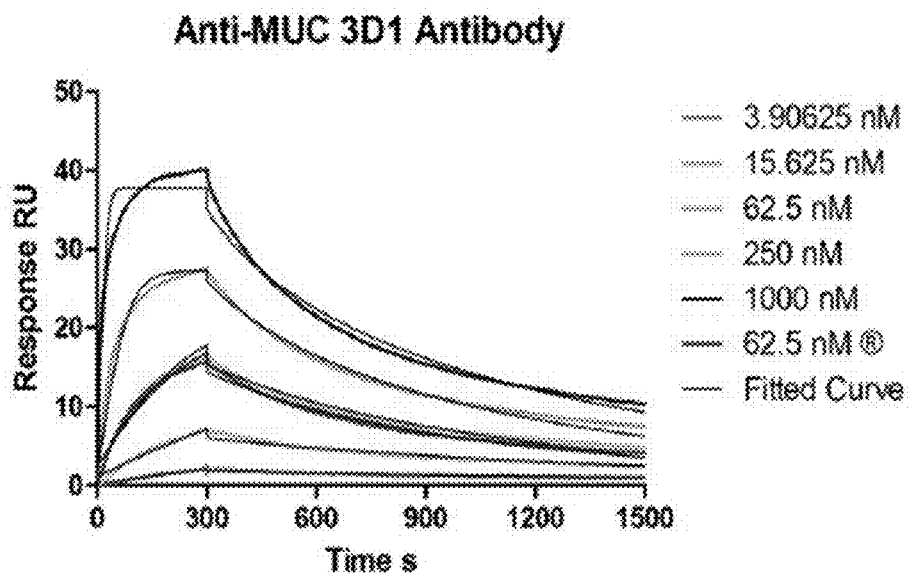
FIG. 6. Affinity determination of parent 3D1 antibody using Biacore T200. The Chi$_2$ value (<10% R$_{max}$) and U-value (<15) of the fitting indicate reliable fit.

Affinity ranking data of 25 humanized antibodies were shown in Table 2 and FIG. 6. The top 12 humanized antibodies that showed better or comparable kd values compared with the chimeric antibody were selected for FACS titration.

Figure 7:
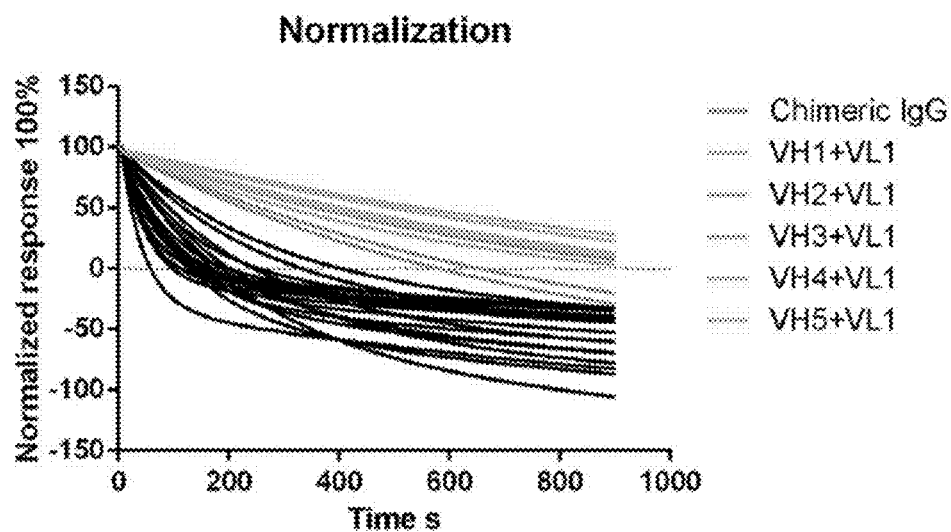
FIG. 7. Affinity ranking of humanized antibodies using Biacore T200.

The geometric mean and $EC_{50}$ of the 12 selected humanized antibodies analyzed by FACS titration were shown in FIG. 7 and Table 3.

Summary. In this project, a mouse antibody was humanized using a CDR grafting method. The four top humanized antibodies showed comparable binding affinity with chimeric antibody were identified: VH3+VL1, VH5+VL1, VH1+VL1 and VH2+VL1.

TABLE 1

Amount and concentration data of 25 purified humanized antibodies

| NO | Sample | Conc. (mg/ml) | Amount (mg) |
|---|---|---|---|
| 1 | VH1 + VL1 | 1.372 | 1.372 |
| 2 | VH1 + VL2 | 0.891 | 0.356 |
| 3 | VH1 + VL3 | 2.304 | 0.922 |
| 4 | VH1 + VL4 | 1.475 | 0.590 |
| 5 | VH1 + VL5 | 1.872 | 0.374 |
| 6 | VH2 + VL1 | 1.030 | 1.030 |
| 7 | VH2 + VL2 | 0.972 | 0.097 |
| 8 | VH2 + VL3 | 1.009 | 0.404 |
| 9 | VH2 + VL4 | 1.002 | 0.401 |
| 10 | VH2 + VL5 | 0.990 | 0.198 |
| 11 | VH3 + VL1 | 1.168 | 1.168 |
| 12 | VH3 + VL2 | 0.212 | 0.042 |
| 13 | VH3 + VL3 | 1.022 | 0.409 |
| 14 | VH3 + VL4 | 1.563 | 0.313 |
| 15 | VH3 + VL5 | 0.492 | 0.049 |
| 16 | VH4 + VL1 | 1.373 | 10.294 |
| 17 | VH4 + VL2 | 1.359 | 0.408 |
| 18 | VH4 + VL3 | 1.818 | 1.818 |
| 19 | VH4 + VL4 | 1.616 | 0.760 |
| 20 | VH4 + VL5 | 1.425 | 0.285 |
| 21 | VH5 + VL1 | 1.511 | 3.022 |
| 22 | VH5 + VL2 | 1.739 | 0.574 |
| 23 | VH5 + VL3 | 1.435 | 1.435 |
| 24 | VH5 + VL4 | 1.330 | 0.439 |
| 25 | VH5 + VL5 | 1.806 | 0.379 |

TABLE 2

Kinetic data of selected humanized antibodies to antigen protein using Biacore T200

| Ligand | Analyte | kd (1/s) | Rmax (RU) | $Chi^2$ ($RU^2$) |
|---|---|---|---|---|
| VH3 + VL1 | MUC-SEA-His | 1.50E-03 | 56.8 | 0.771 |
| VH5 + VL1 | MUC-SEA-His | 1.92E-03 | 51.5 | 1.08 |
| VH2 + VL1 | MUC-SEA-His | 1.33E-03 | 51.1 | 0.373 |
| VH4 + VL1 | MUC-SEA-His | 2.61E-03 | 46.9 | 1.29 |
| VH1 + VL1 | MUC-SEA-His | 2.10E-03 | 52.9 | 1.08 |
| Chimeric IgG | MUC-SEA-His | 2.21E-03 | 55.1 | 1.7 |
| Chimeric IgG | MUC-SEA-His | 2.24E-03 | 59.3 | 2.09 |
| Chimeric IgG | MUC-SEA-His | 4.25E-03 | 48.9 | 18.8 |
| VH2 + VL4 | MUC-SEA-His | 7.41E-03 | 67.1 | 51.8 |
| VH5 + VL3 | MUC-SEA-His | 1.64E-02 | 52.4 | 196 |
| VH3 + VL4 | MUC-SEA-His | 9.02E-03 | 76.2 | 122 |
| VH2 + VL3 | MUC-SEA-His | 1.24E-02 | 53.1 | 133 |
| VH3 + VL3 | MUC-SEA-His | 1.52E-02 | 59.5 | 272 |
| VH1 + VL4 | MUC-SEA-His | 1.24E-02 | 66.8 | 69.5 |
| VH5 + VL4 | MUC-SEA-His | 1.79E-02 | 62.1 | 524 |
| VH4 + VL3 | MUC-SEA-His | 2.37E-02 | 49.5 | 137 |
| VH4 + VL4 | MUC-SEA-His | 2.43E-02 | 60.5 | 371 |
| VH1 + VL3 | MUC-SEA-His | 2.25E-02 | 55.3 | 197 |
| VH2 + VL2 | MUC-SEA-His | 1.66E-02 | 66 | 56 |
| VH5 + VL2 | MUC-SEA-His | 2.28E-02 | 56.9 | 64.5 |
| VH3 + VL2 | MUC-SEA-His | 1.95E-02 | 74.1 | 109 |
| VH5 + VL5 | MUC-SEA-His | 2.07E-02 | 62.6 | 61.3 |
| VH4 + VL2 | MUC-SEA-His | 3.15E-02 | 61.6 | 45.1 |
| VH2 + VL5 | MUC-SEA-His | 1.93E-02 | 69.3 | 85.7 |
| VH1 + VL2 | MUC-SEA-His | 2.94E-02 | 66.9 | 68.8 |
| VH3 + VL5 | MUC-SEA-His | 2.30E-02 | 80.2 | 174 |
| VH1 + VL5 | MUC-SEA-His | 3.02E-02 | 70.7 | 76.5 |
| VH4 + VL5 | MUC-SEA-His | 5.78E-02 | 58.8 | 207 |

TABLE 3

The geometric means of 12 selected humanized antibodies by FACS titration

| Conc. (nM) | VH1 + VL1 | VH1 + VL4 | VH2 + VL1 | VH2 + VL3 | VH2 + VL4 | VH3 + VL1 | VH3 + VL3 | VH3 + VL4 | VH4 + VL1 | VH5 + VL1 | VH5 + VL3 | VH5 + VL4 | Chimeric IgG |
|---|---|---|---|---|---|---|---|---|---|---|---|---|---|
| 500 | 351 | 141 | 342 | 178 | 212 | 334 | 148 | 235 | 253 | 316 | 170 | 199 | 284 |
| 250 | 363 | 142 | 337 | 167 | 216 | 321 | 154 | 227 | 250 | 327 | 167 | 193 | 289 |
| 125 | 332 | 132 | 306 | 147 | 188 | 305 | 151 | 208 | 225 | 326 | 126 | 202 | 275 |
| 62.5 | 290 | 111 | 265 | 124 | 161 | 263 | 134 | 171 | 188 | 291 | 141 | 190 | 248 |
| 31.25 | 185 | 73.3 | 126 | 60.4 | 74.6 | 192 | 77.2 | 130 | 113 | 219 | 110 | 152 | 159 |
| 15.625 | 68.7 | 27.7 | 29 | 26.2 | 28.4 | 71.3 | 27.3 | 54.6 | 27 | 91.2 | 61.5 | 67.1 | 90.8 |
| 7.812 | 23.1 | 6.83 | 6.37 | 11.8 | 19 | 36 | 7.91 | 22.2 | 8.87 | 29.7 | 31 | 28.6 | 39.5 |
| 3.906 | 9.54 | 4.1 | 5.23 | 4.03 | 9.37 | 16.3 | 5.77 | 12 | 4.22 | 20 | 15.5 | 15.3 | 18.1 |
| 1.953 | 5.68 | 3.16 | 4.38 | 3.25 | 5.22 | 11.4 | 3.64 | 19 | 2.94 | 7.02 | 8.05 | 5.71 | 10.1 |
| 0.977 | 3.17 | 2.86 | 3.68 | 2.83 | 3.76 | 6.94 | 2.95 | 25.6 | 2.51 | 4.25 | 4.13 | 4.01 | 5.16 |
| 0.488 | 3 | 2.85 | 3.27 | 2.74 | 3.16 | 3.81 | 2.65 | 19.5 | 2.54 | 2.93 | 3.27 | 3.52 | 3.48 |
| 0.244 | 2.72 | 2.82 | 3 | 2.73 | 2.88 | 3.1 | 2.61 | 9.23 | 2.54 | 2.67 | 2.82 | 2.84 | 3.14 |
| EC50 (nM) | 30.34 | 31.89 | 58.65 | 45.37 | 41.28 | 28.68 | 30.89 | 33.1 | 36.65 | 23.61 | 21.86 | 20.61 | 26.53 |

Example 2

ADC Data with Humanized 3D1 Anti-MUC1-C/ECD Mab

Generation of ADCs. Humanized-3D1 (h3D1) antibody conjugated to the cytotoxic drug monomethyl auristatin E (MMAE) with a cleavable linker was generated. To compare the effects of h3D1-MMAE, the inventors also generated mouse-3D1 (m3D1)-MMAE. Two different preparations of m3D1 and h3D1-MMAEs (Moradec vs. Abzena) were generated to compare the effects. To test another toxin linked to h3D1, h3D1 was also linked with Abzena Toxin 1005.

Cell Proliferation/Viability Assay. The effects of these different versions of ADC conjugates on tumor cell viability were assessed using Alamar Blue reagent. 1500 to 4000 HCT-116/MUC1 or HCT-116/Vector cells/well were plated in 96-well plates and allowed to adhere overnight at 37° C., 5% $CO_2$. Cells were treated with different preparations of 3D1-ADCs for 5 days, starting from 240 nM with 3-fold serial dilutions for eight concentrations. Alamar Blue reagent (1:10 dilution in the culture medium) was added to the wells and incubated for 2-4 hours and the change in absorption was measured with excitation at 570 nM and emission at 600 nM. The percentage viability was calculated compared to the untreated control as 100%. The dose response curve was plotted as a 4-parameter logistic curve with GraphPad Prism (GraphPad software, La Jolla, Calif.) and the $IC_{50}$ value was deduced from the curve.

Figure 15:
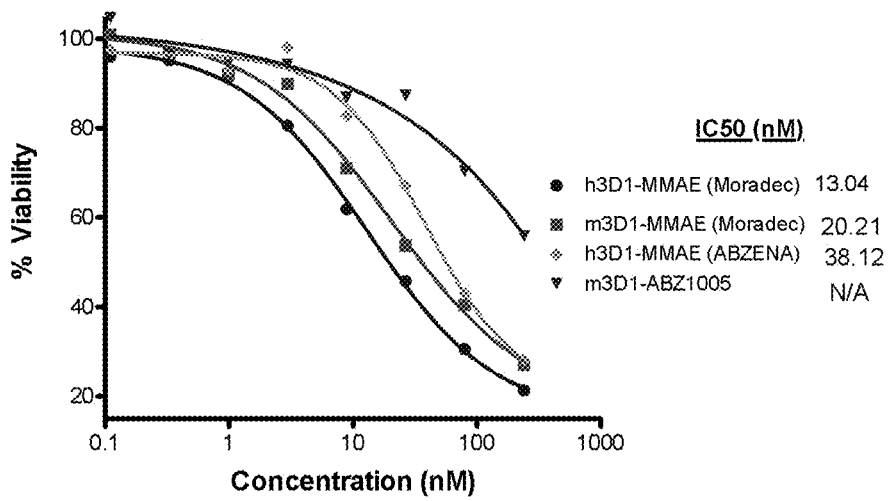
FIGS. 15-16. Untreated HCT-116/vector cells (FIG. 16), and treated HCT-116/MUC1 cells with all different versions (with mouse and humanized 3D1) (FIG. 15), with only the latter showing ADC is associated with significant killing.
Figure 16:
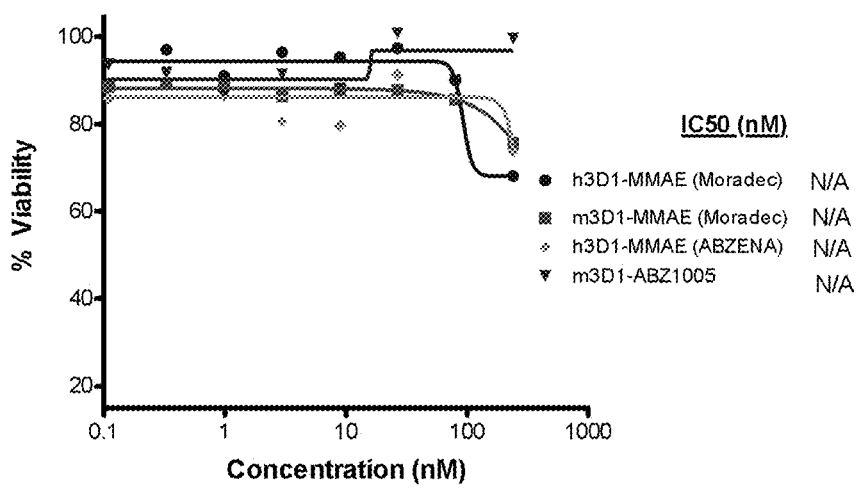

Results. The results demonstrate that, in contrast to HCT-116/vector cells (FIG. 16), treatment of HCT-116/MUC1 cells with all different versions (with mouse and humanized 3D1) of ADCs is associated with significant killing (FIG. 15). These results indicate MUC1-specific killing with both mouse and humanized anti-MUC1-C/ECD antibody-ADCs.

\* \* \*

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,683,202
U.S. Pat. No. 4,684,611
U.S. Pat. No. 4,816,567
U.S. Pat. No. 4,867,973
U.S. Pat. No. 4,879,236
U.S. Pat. No. 4,938,948
U.S. Pat. No. 4,952,500
U.S. Pat. No. 5,021,236
U.S. Pat. No. 5,141,648
U.S. Pat. No. 5,196,066
U.S. Pat. No. 5,217,879
U.S. Pat. No. 5,302,523
U.S. Pat. No. 5,322,783
U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,563,250
U.S. Pat. No. 5,565,332
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,856,456
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,880,270
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
U.S. patent Ser. No. 12/789,127
U.S. patent Ser. No. 13/026,858
U.S. patent Ser. No. 13/045,033
"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Allred et al., *Arch. Surg.*, 125(1), 107-113, 1990.
Almendro et al., *J. Immunol.*, 157(12):5411-5421, 1996.
Amado and Chen, *Science*, 285(5428):674-676, 1999.

Angel et al., *Cell,* 49:729, 1987a.
Angel et al., *Cell,* 49:729, 1987b.
Armentano et al., *Proc. Natl. Acad. Sci. USA,* 87(16):6141-6145, 1990.
Atchison and Perry, *Cell,* 46:253, 1986.
Atchison and Perry, *Cell,* 48:121, 1987.
Atherton et al., *Biol. of Reproduction,* 32, 155-171, 1985.
Ausubel et al., *Current Protocols in Molecular Biology,* Greene Publishing Associates and Wiley Interscience, N.Y., 1994.
Baldus et al., *Clin. Cancer Res.,* 10(8):2790-2796, 2004.
Banerji et al., *Cell,* 27:299, 1981.
Banerji et al., *Cell,* 33(3):729-740, 1983.
Bates, *Mol. Biotechnol.,* 2(2): 135-145, 1994.
Batra et al., *Am. J. Respir. Cell Mol. Biol.,* 21(2):238-245, 1999.
Battraw and Hall, *Theor. App. Genet.,* 82(2):161-168, 1991.
Beidler et al., *J. Immunol.,* 141(11):4053-4060, 1988.
Berkhout et al., *Cell,* 59:273-282, 1989.
Bett et al., *J. Virololgy,* 67(10):5911-5921, 1993.
Bhattacharjee et al., *J. Plant Bioch. Biotech.,* 6(2):69-73. 1997.
Bilbao et al., *FASEB J.,* 11(8):624-634, 1997.
Blackwell et al., *Arch. Otolaryngol Head Neck Surg.,* 125 (8):856-863, 1999.
Blanar et al., *EMBO J.,* 8:1139, 1989.
Blomer et al., *J. Virol.,* 71(9):6641-6649, 1997.
Bodine and Ley, *EMBO J.,* 6:2997, 1987.
Boshart et al., *Cell,* 41:521, 1985.
Bosze et al., *EMBO J.,* 5(7):1615-1623, 1986.
Braddock et al., *Cell,* 58:269, 1989.
Brown et al., *J. Immunol. Meth.,* 12; 130(1):111-121, 1990.
Bulla and Siddiqui, *J. Virol.,* 62:1437, 1986.
Campbell and Villarreal, *Mol. Cell. Biol.,* 8:1993, 1988.
Campbell, In: *Monoclonal Antibody Technology, Laboratory Techniques in Biochemistry and Molecular Biology,* Vol. 13, Burden and Von Knippenberg, Eds. pp. 75-83, Amsterdam, Elsevier, 1984.
Campere and Tilghman, *Genes and Dev.,* 3:537, 1989.
Campo et al., *Nature,* 303:77, 1983.
Capaldi et al., *Biochem. Biophys. Res. Comm.,* 74(2):425-433, 1977.
Caplen et al., *Gene Ther.,* 6(3):454-459, 1999.
Carbonelli et al., *FEMS Microbiol. Lett.,* 177(1):75-82, 1999.
Case et al., *Proc. Natl. Acad. Sci. USA,* 96(6):2988-2993, 1999.
Celander and Haseltine, *J. Virology,* 61:269, 1987.
Celander et al., *J. Virology,* 62:1314, 1988.
Chandler et al., *Proc. Natl. Acad. Sci. USA,* 94(8):3596-601, 1997.
Chang et al., *Mol. Cell. Biol.,* 9:2153, 1989.
Chatterjee et al., *Proc. Natl. Acad. Sci. USA,* 86:9114, 1989.
Chen and Okayama, *Mol. Cell Biol.,* 7(8):2745-2752, 1987.
Chillon et al., *J. Virol.,* 73(3):2537-2540, 1999.
Choi et al., *J. Mol. Biol.,* 262(2):151-167, 1996.
Christou et al., *Proc. Natl. Acad. Sci. USA,* 84(12):3962-3966, 1987.
Clay et al., *J. Immunol.,* 162:1749, 1999.
Cocea, *Biotechniques,* 23(5):814-816, 1997.
Coffey et al., *Science,* 282(5392):1332-1334, 1998.
Cohen et al., *J. Cell. Physiol.,* 5:75, 1987.
Costa et al., *Mol. Cell. Biol.,* 8:81-90, 1988.
Cripe et al., *EMBO J.,* 6:3745, 1987.
Culotta and Hamer, *Mol. Cell. Biol.,* 9:1376-1380, 1989.
D'Halluin et al., *Plant Cell,* 4(12):1495-1505, 1992.
Dandolo et al., *J. Virology,* 47:55-64, 1983.
De Jager et al., *Semin. Nucl. Med.* 23(2), 165-179, 1993.
DeLuca et al., *J. Virol.,* 56(2):558-570, 1985.
Derby et al., *Hear Res,* 134(1-2):1-8, 1999.
Deschamps et al., *Science,* 230:1174-1177, 1985.
Dholakia et al., *J. Biol. Chem.,* 264, 20638-20642, 1989.
Doolittle and Ben-Zeev, *Methods Mol. Biol.,* 109, 215-237, 1999.
Dorai et al., *Int. J. Cancer,* 82(6):846-52, 1999.
Duraisamy et al., *Gene,* 373:28-34, 2006.
Edbrooke et al., *Mol. Cell. Biol.,* 9:1908-1916, 1989.
Edlund et al., *Science,* 230:912-916, 1985.
Engel and Kohn, *Front Biosci,* 4:e26-33, 1999.
EP Application 125,023
EP Application 171,496
EP Application 173,494
EP Application 184,187
EPO 0273085
Fechheimer et al., *Proc Natl. Acad. Sci. USA,* 84:8463-8467, 1987.
Feldman et al., *Cardiovasc. Res.,* 32(2):194-207, 1996.
Feldman et al., *Semin. Interv. Cardiol.,* 1(3):203-208, 1996.
Feng and Holland, *Nature,* 334:6178, 1988.
Feng et al., *Nat. Biotechnol.,* 15(9):866-870, 1997.
Firak and Subramanian, *Mol. Cell. Biol.,* 6:3667, 1986.
Fisher et al., *Hum. Gene Ther.,* 7(17):2079-2087, 1996.
Foecking and Hofstetter, *Gene,* 45(1):101-105, 1986.
Fraley et al., *Proc. Natl. Acad. Sci. USA,* 76:3348-3352, 1979.
Fujita et al., *Cell,* 49:357, 1987.
Fujiwara and Tanaka, *Nippon Geka Gakkai Zasshi,* 99(7): 463-468, 1998.
Garoff and Li, *Curr. Opin. Biotechnol.,* 9(5):464-469, 1998.
Garrido et al., *J. Neurovirol.,* 5(3):280-288, 1999.
Gefter et al., *Somatic Cell Genet.,* 3:231-236, 1977.
Gendler et al., *J. Biol. Chem.,* 263:12820-12823, 1988.
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Gillies et al., *Cell,* 33:717, 1983.
Gloss et al., *EMBO J.,* 6:3735, 1987.
Gnant et al., *Cancer Res.,* 59(14):3396-403, 1999.
Gnant et al., *J. Natl. Cancer Inst.,* 91(20):1744-1750, 1999.
Godbout et al., *Mol. Cell. Biol.,* 8:1169, 1988.
Goding, In: *Monoclonal Antibodies: Principles and Practice,* 2d ed., Orlando, Fla., Academic Press, 60-61, 65-66, 71-74, 1986.
Goodbourn and Maniatis, *Cell,* 41(2):509-520, 1985.
Goodbourn et al., *Cell,* 45:601, 1986.
Gopal, *Mol. Cell Biol.,* 5:1188-1190, 1985.
Graham and Prevec, *Mol Biotechnol,* 3(3):207-220, 1995.
Graham and Van Der Eb, *Virology,* 52:456-467, 1973.
Greene et al., *Immunology Today,* 10:272, 1989.
Grosschedl and Baltimore, *Cell,* 41:885, 1985.
Gulbis and Galand, *Hum. Pathol.* 24(12), 1271-1285, 1993.
Haecker et al., *Hum. Gene Ther.,* 7(15):1907-1914, 1996.
Han et al., *J. Infect. Dis.,* 179:230-233, 1999.
Harland and Weintraub, *J. Cell Biol.,* 101(3):1094-1099, 1985.
Haslinger and Karin, *Proc. Natl. Acad. Sci. USA,* 82:8572, 1985.
Hauber and Cullen, *J. Virology,* 62:673, 1988.
Hayashi et al., *Neurosci. Lett.,* 267(1):37-40, 1999.
He et al., *Plant Cell Reports,* 14 (2-3):192-196, 1994.
Hen et al., *Nature,* 321:249, 1986.
Hensel et al., *Lymphokine Res.,* 8:347, 1989.
Hermens and Verhaagen, *Prog. Neurobiol.,* 55(4):399-432, 1998.

Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Holzer et al. *Virology*, 253(1): 107-114, 1999.
Horlick and Benfield, *Mol. Cell. Biol.*, 9:2396, 1989.
Hou and Lin, *Plant Physiology*, 111:166, 1996.
Howard et al., *Ann. NY Acad. Sci.*, 880:352-365, 1999.
Huang et al., *Cell*, 27:245, 1981.
Huard et al., *Neuromuscul Disord*, 7(5):299-313, 1997.
Hug et al., *Mol. Cell. Biol.*, 8:3065-3079, 1988.
Hwang et al., *Mol. Cell. Biol.*, 10:585, 1990.
Imagawa et al., *Cell*, 51:251, 1987.
Imai et al., *Nephrologie*, 19(7):397-402, 1998.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Irie et al., *Antisense Nucleic Acid Drug Dev.*, 9(4):341-349, 1999.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9(8):3393-3399, 1989.
Johnston et al., *J. Virol.*, 73(6):4991-5000, 1999.
Jones et al., *Nature*, 321:522-525, 1986.
Kadesch and Berg, *Mol. Cell. Biol.*, 6:2593, 1986.
Kaeppler et al., *Plant Cell Rep.*, 8:415-418, 1990.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kaufman et al., *Arch. Ophthalmol.*, 117(7):925-928, 1999.
Kawamoto et al., *Mol. Cell. Biol.*, 8:267, 1988.
Kay, *Haemophilia*, 4(4):389-392, 1998.
Khatoon et al., *Ann. of Neurology*, 26, 210-219, 1989.
Kiledjian et al., *Mol. Cell. Biol.*, 8:145, 1988.
King et al., *J. Biol. Chem.*, 269, 10210-10218, 1989.
Kinlough et al., *J. Biol. Chem.*, 279(51):53071-53077, 2004.
Kinoshita et al., *Biochem. Biophys. Res. Commun.*, 394:205-210, 2010.
Klamut et al., *Mol. Cell. Biol.*, 10:193, 1990.
Klimatcheva et al., *Front Biosci*, 4:D481-496, 1999.
Koch et al., *Mol. Cell. Biol.*, 9:303, 1989.
Kohler and Milstein, *Eur. J. Immunol.*, 6, 511-519, 1976.
Kohler and Milstein, *Nature*, 256, 495-497, 1975.
Kohut et al., *Am. J. Physiol.*, 275(6Pt1):L1089-1094, 1998.
Kooby et al., *FASEB J*, 13(11):1325-34, 1999.
Kraus et al. *FEBS Lett.*, 428(3): 165-170, 1998.
Kriegler and Botchan, *Mol. Cell. Biol.*, 3:325, 1983.
Kriegler et al., *Cell*, 38:483, 1984a.
Kriegler et al., *In: Cancer Cells 2/Oncogenes and Viral Genes*, Van de Woude et al. eds, Cold Spring Harbor, Cold Spring Harbor Laboratory, 1984b.
Krisky et al., *Gene Ther*, 5(11):1517-1530, 1998a.
Krisky et al., *Gene Ther*, 5(12):1593-1603, 1998b.
Kuhl et al., *Cell*, 50:1057, 1987.
Kunz et al., *Nucl. Acids Res.*, 17:1121, 1989.
Kyte and Doolittle, *J. Mol. Biol.*, 157(1):105-132, 1982.
Lachmann and Efstathiou, *Curr. Opin. Mol. Ther.*, 1(5):622-632, 1999.
Lareyre et al., *J. Biol. Chem.*, 274(12):8282-8290, 1999.
Larsen et al., *Proc. Natl. Acad. Sci. USA*, 83:8283, 1986.
Laspia et al., *Cell*, 59:283, 1989.
Latimer et al., *Mol. Cell. Biol.*, 10:760, 1990.
Lazzeri, *Methods Mol. Biol.*, 49:95-106, 1995.
Lee et al., *Environ. Mol. Mutagen.*, 13(1):54-59, 1989.
Lee et al., *Nature*, 294:228, 1981.
Lee et al., *Nucleic Acids Res.*, 12:4191-206, 1984.
Lee et al., *DNA Cell Biol.*, 16(11):1267-1275, 1997.
Leibowitz et al., *Diabetes*, 48(4):745-753, 1999.
Lesch, *Biol Psychiatry*, 45(3):247-253, 1999.
Levenson et al., *Hum. Gene Ther.*, 9(8):1233-1236, 1998.
Li et al., *Cancer Biol. Ther.*, 2:187-193, 2003b.
Lin et al., *Mol. Cell. Biol.*, 10:850, 1990.
Lundstrom, *J. Recept Signal Transduct. Res.*, 19(1-4):673-686, 1999.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Marienfeld et al., *Gene Ther.*, 6(6):1101-1113, 1999.
Mastrangelo et al., *Biotechnol. Bioeng.*, 65(3):298-305, 1999.
McNeall et al., *Gene*, 76:81, 1989.
Miksicek et al., *Cell*, 46:203, 1986.
Miller et al., *J. Pharmacol. Exp. Ther.*, 264:11-16, 1993.
Miyatake et al., *Gene Ther.*, 6:564-572, 1999.
Moldawer et al., *Shock*, 12(2):83-101, 1999.
Mordacq and Linzer, *Genes and Dev.*, 3:760, 1989.
Moreau et al., *Nucl. Acids Res.*, 9:6047, 1981.
Moriuchi et al., *Cancer Res*, 58(24):5731-5737, 1998.
Morrison et al., *J. Gen. Virol.*, 78(Pt 4):873-878, 1997.
Morrison, *Science*, 229(4719):1202-1207, 1985.
Muesing et al., *Cell*, 48:691, 1987.
Nakamura et al., *In: Enzyme Immunoassays: Heterogeneous and Homogeneous Systems*, Chapter 27, 1987.
Naldini et al., *Science*, 272(5259):263-267, 1996.
Neuberger et al., *Nucleic Acids Res.*, 16(14B):6713-6724, 1988.
Neumann et al., *Proc. Natl. Acad. Sci. USA*, 96(16):9345-9350, 1999.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Omirulleh et al., *Plant Mol. Biol.*, 21(3):415-428, 1993.
Omitz et al., *Mol. Cell. Biol.*, 7:3466, 1987.
Ondek et al., *EMBO J.*, 6:1017, 1987.
O'Shannessy et al., *J. Immun. Meth.*, 99, 153-161, 1987.
Owens and Haley, *J. Biol. Chem.*, 259, 14843-14848, 1987.
Palmiter et al., *Cell*, 29:701, 1982.
Parks et al., *J. Virol.*, 71(4):3293-8, 1997.
PCT Application PCT/US86/02269
PCT Application WO 86/01533
PCT Appln. WO 92/17598
PCT Appln. WO 94/09699
PCT Appln. WO 95/06128
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur Respir J*, 11(2):492-497, 1998.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Posner et al., *Hybridoma* 6, 611-625, 1987.

Potrykus et al., *Mol. Gen. Genet.*, 199(2):169-177, 1985.
Potter and Haley, *Meth. Enzymol.*, 91, 613-633, 1983.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Rabinovitch et al., *Diabetes*, 48(6): 1223-1229, 1999.
Reddy et al., *Virology*, 251(2):414-26, 1998.
Redondo et al., *Science*, 247:1225, 1990.
Reisman and Rotter, *Mol. Cell. Biol.*, 9:3571, 1989.
Remington's Pharmaceutical Sciences, 15$^{th}$ Ed., 33:624-652, 1990.
Resendez Jr. et al., *Mol. Cell. Biol.*, 8:4579, 1988.
Rhodes et al., *Methods Mol. Biol.*, 55:121-131, 1995.
Rippe et al., *Mol. Cell. Biol.*, 9(5):2224-22277, 1989.
Rippe, et al., *Mol. Cell Biol.*, 10:689-695, 1990.
Rittling et al., *Nucl. Acids Res.*, 17:1619, 1989.
Robbins and Ghivizzani, *Pharmacol Ther*, 80(1):35-47, 1998.
Robbins et al., *Trends Biotechnol.*, 16(1):35-40, 1998.
Sambrook et al., In: *Molecular cloning: a laboratory manual*, 2$^{nd}$ Ed., Cold Spring Harbor Laboratory Press, Cold Spring Harbor, N.Y., 1989.
Sawai et al. *Mol. Genet. Metab.*, 67(1):36-42, 1999.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shaw et al., *J. Natl. Cancer Inst.*, 80(19):1553-1559, 1988.
Sherman et al., *Mol. Cell. Biol.*, 9:50, 1989.
Sleigh and Lockett, *J. EMBO*, 4:3831, 1985.
Smith et al., *Neuron.*, 20:1093-1102, 1998.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stewart et al., *Arch. Biochem. Biophys.* 365:71-74; 1999.
Stuart et al., *Nature*, 317:828, 1985.
Sullivan and Peterlin, *Mol. Cell. Biol.*, 7:3315, 1987.
Sun et al., *J. Steroid Biochem.*, 26(1):83-92, 1987.
Suzuki et al., *Biochem Biophys Res Commun*, 252(3):686-90, 1998.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Timiryasova et al., *Int. J. Oncol.*, 14(5):845-854, 1999.
Treisman, *Cell*, 42:889, 1985.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell Biol.*, 6:716-718, 1986.
Tyndall et al., *Nuc. Acids. Res.*, 9:6231, 1981.
Vanderkwaak et al., *Gynecol Oncol*, 74(2):227-234, 1999.
Vasseur et al., *Proc. Natl. Acad. Sci. USA*, 77:1068, 1980.
Verhoeyen et al., *Science*, 239(4847):1534-1536, 1988.
Wagner et al., *Proc. Natl. Acad. Sci. USA* 87(9):3410-3414, 1990.
Wang and Calame, *Cell*, 47:241, 1986.
Wang et al., *Infect. Immun.*, 66:4193-202, 1998.
Wawrzynczak & Thorpe, *Cancer Treat Res.*, 37:239-51, 1988.
Weber et al., *Cell*, 36:983, 1984.
Wei et al., *Cancer Cell*, 7:167-178, 2005.
Weihl et al., *Neurosurgery*, 44(2):239-252, 1999.
Wen et al., *J. Biol. Chem.*, 278:38029-38039, 2003.
White et al. *J. Virol.*, 73(4):2832-2840, 1999.
Wilson, *J. Clin. Invest.*, 98(11):2435, 1996.
Winoto and Baltimore, *Cell*, 59:649, 1989.
Wong et al., *Gene*, 10:87-94, 1980.
Wood et al., *J. Clin. Lab. Immunol.*, 17(4):167-171, 1985.
Wu and Wu, *Adv. Drug Delivery Rev.*, 12:159-167, 1993.
Wu and Wu, *J. Biol. Chem.*, 262:4429-4432, 1987.
Wu et al., *Biochem. Biophys. Res. Commun.*, 233(1):221-226, 1997.
Wu et al., *Cancer Res.*, 58(8): 1605-8, 1998.
Yamada et al., *Brain Res.*, 833(2):302-307, 1999.
Yeung et al., *Gene Ther.*, 6(9):1536-1544, 1999.
Yoon et al., *J. Gastrointest. Surg.*, 3(1):34-48, 1999.
Yutzey et al. *Mol. Cell. Biol.*, 9:1397, 1989.
Zhao-Emonet et al., *Biochim. Biophys. Acta*, 1442(2-3):109-119, 1998.
Zheng et al., *J. Gen. Virol.*, 80(Pt 7): 1735-1742, 1999.
Zhou et al., *Nature*, 361(6412):543-547, 1993.
Zufferey et al., *Nat. Biotechnol.*, 15(9):871-875, 1997.

What is claimed is:

1. An antibody or an antigen-binding fragment thereof that binds selectively to a conformational epitope from MUC1-C extracellular domain (MUC1-C/ECD) defined by SEQ ID NO: 1, wherein said antibody or antigen binding fragment comprises a variable light domain sequence of SEQ ID NO: 2, and a variable heavy domain sequence of SEQ ID NO: 6.

2. The antibody or antigen-binding fragment of claim 1, wherein said antibody is a single chain antibody.

3. The antibody or antigen-binding fragment of claim 1, wherein said antibody is a chimeric antibody.

4. The antibody or antigen-binding fragment of claim 1, wherein said antibody fragment is a Fab fragment.

5. The antibody or antigen-binding fragment of claim 1, wherein said antibody is a recombinant antibody or antigen binding fragment having specificity for the conformational epitope in MUC1-C/ECD and a distinct cancer cell surface antigen.

6. The antibody or antigen-binding fragment of claim 1, wherein said antibody is an IgG.

7. The antibody or antigen-binding fragment of claim 1, wherein said antibody further comprises a label.

8. The antibody or antigen-binding fragment of claim 7, wherein said label is a peptide tag, an enzyme, a magnetic particle, a chromophore, a fluorescent molecule, a chemiluminescent molecule, or a dye.

9. The antibody or antigen-binding fragment of claim 1, wherein said antibody or fragment further comprises an antitumor drug linked thereto.

10. The antibody or antigen-binding fragment of claim 9, wherein said antitumor drug is linked to said antibody or fragment through a photolabile linker.

11. The antibody or antigen-binding fragment of claim 10, wherein said antitumor drug is linked to said antibody or fragment through an enzymatically-cleaved linker.

12. The antibody or antigen-binding fragment of claim 10, wherein said antitumor drug is a toxin, a radioisotope, a cytokine or an enzyme.

13. The antibody or antigen-binding fragment of claim 1, wherein said antibody or fragment is conjugated to a nanoparticle or a liposome.

14. The antibody or antigen-binding fragment of claim 1, wherein said antibody induces MUC1-positive tumor cell death, such as by antibody-dependent cytotoxicity, antibody-dependent cell cytotoxicity or complement-mediated cytoxocity.

15. A fusion protein comprising:
(i) an antibody that binds selectively to a conformational epitope in MUC1-C extracellular domain (MUC1-C/ECD) defined by SEQ ID NO: 1, wherein said antibody comprises a variable light domain sequence of SEQ ID NO: 2, and a variable heavy domain sequence of SEQ ID NO: 6; and
(ii) a second single chain antibody that binds to a T or B cell.

16. A chimeric antigen receptor comprising:
(i) an ectodomain comprising single chain antibody variable region that binds selectively to a conformational epitope in MUC1-C/extracellular domain (MUC1-C/ECD) defined by SEQ ID NO: 1, wherein said antibody comprises a variable light domain sequence of SEQ ID NO: 2, and a variable heavy domain sequence of SEQ ID NO: 6, with a flexible hinge attached at the C-terminus of said single chain antibody variable region;
(ii) a transmembrane domain; and
(iii) an endodomain,
wherein said endodomain comprises a signal transduction function when said single-chain antibody variable region is engaged with MUC 1.

* * * * *